US008614341B2

(12) United States Patent
Rovati et al.

(10) Patent No.: US 8,614,341 B2
(45) Date of Patent: Dec. 24, 2013

(54) AMORPHOUS SILIBININ FOR THE TREATMENT OF VIRAL HEPATITIS

(75) Inventors: Lucio Claudio Rovati, Monza (IT); Astrid Nagell, Hamburg (DE); Aguirre Jaime Xiol, Barcelona (ES); Prous Santiago Rull, Barcelona (ES); Ralf-Torsten Pohl, Speyer (DE); Ulrich Mengs, Rösrath (DE)

(73) Assignee: Euromed S.A., Mottet del Valles (ES)

( * ) Notice: Subject to any disclaimer, the term of this patent is extended or adjusted under 35 U.S.C. 154(b) by 0 days.

(21) Appl. No.: 13/320,176

(22) PCT Filed: May 14, 2010

(86) PCT No.: PCT/EP2010/002978
§ 371 (c)(1),
(2), (4) Date: Jan. 12, 2012

(87) PCT Pub. No.: WO2010/130460
PCT Pub. Date: Nov. 18, 2010

(65) Prior Publication Data
US 2012/0108825 A1 May 3, 2012

(30) Foreign Application Priority Data

May 14, 2009 (EP) .................................. 09160322
May 18, 2009 (EP) .................................. 09006663
May 20, 2009 (EP) .................................. 09006804

(51) Int. Cl.
*C07D 319/14* (2006.01)
(52) U.S. Cl.
USPC ........................................................ 549/362
(58) Field of Classification Search
USPC ........................................................ 549/362
See application file for complete search history.

(56) References Cited

U.S. PATENT DOCUMENTS

| 3,636,353 | A | 1/1972 | Untermyer |
| 4,368,195 | A | 1/1983 | Madus et al. |
| 4,871,763 | A | 10/1989 | Madaus et al. |
| 5,607,614 | A | 3/1997 | Kawano et al. |
| 5,906,991 | A | 5/1999 | Waechter et al. |
| 2011/0027396 | A1* | 2/2011 | Nagell et al. ................. 424/764 |

FOREIGN PATENT DOCUMENTS

| CA | 1029735 | 4/1978 |
| DE | 1923983 | 11/1969 |
| DE | 1767666 | 9/1971 |
| DE | 2914330 | 10/1980 |
| EP | 0422497 | 4/1991 |
| EP | 0722918 | 7/1996 |
| EP | 1021198 | 7/2000 |
| GB | 2167414 | 5/1986 |

| WO | 9918985 | 4/1999 |
| WO | 2009 062737 | 5/2009 |
| WO | 2009 080006 | 7/2009 |

OTHER PUBLICATIONS

Lee et al., "Moledcular Structure and Sterochemistry of Silybin A, Silybin B, Isosilybin A, and Isosilybin B, Isolated From *Silybum marianum* (Milk Thistle)", Journal of Natural Products, American Chemical Society, US, vol. 66, No. 9, Sep. 1, 2003, pp. 1171-1174 (XP009121703).
Zhang et al., "Preparation and Characterization of Solid Lipid Nanoparticles Containing Silibinin," Drug Delivery Aug. 2007, vol. 14, No. 1, pp. 381-387 (XP009121783).
Graf et al., "Gram-Scale Purification of Flavonolignan Diastereoisomers From *Silybum marianum* (Milk Thistle) Extract in Support of Preclinical In Vivo Studies for Prostate Cancer Chemoprevention," Planta Medica No. 2007, vol. 73, No. 14, Nov. 2007, pp. 1495-1501 (XP002542801).
Yu, "Amorphous Pharmaceutical Solids: Preparation, Characterization and Stablization," Advanced Drug Delivery Reviews, Elsevier BV, Amsterdam, NL, vol. 48, No. 1, May 16, 2001, pp. 27-42 (XP009065056).
Mayer et al., "Silymarin Treatment of Viral Hepatitis: A Systematic Review," Journal of Viral Hepatitis, Blackwell Publishing Ltd, Oxford, UK, Nov. 1, 2005, pp. 559-567 (XP002477921).
Chavez, "Treatment of Hepatitis C With Milk Thistle?" Journal of Herbal Pharmacotherapy, Haworth Herbal Press, Binghamton, US, vol. 1, No. 3 (Jan. 1, 2001), pp. 79-90 (XP009047629).
Neumann et al., "Succesful Prevention of Hepatits C Virus (HCV) Liver Graft Reinfection by Silibinin Mono-Therapy," Journal of Hepatology—Letters to the Editor, 2010, vol. 52, pp. 951-954.
Beinhardt et al., "Silibinin Monotherapy Prevents Graft Infection After Orthotopic Liver Transplanation in a Patient With Chronic Hepatitis C," Journal of Hepatology—Letter to the Editor, DOI: 10.1016/j:jhep.2010.09-009.
Berg et al., "Silibinin in Hepatitis C Related Liver Transplantation," Journal of Hepatology—Reply to Letter to the Editor, DOI:10.1016/j.jhep.2010.09.009.
International Search Report issued Jul. 26, 2010 in corresponding Application No. PCT/EP2010/002978.
U.P. Neumann et al. "Successful Prevention of Hepatitis C Virus (HCV) Liver Graft Reinfection by Silibinin Mono-Therapy," Journal of Hepatology (2010) vol. 52, pp. 951-954.
Tian-Ming Ding et al. "Determination of Active Component in Silymarin by RP-LC and LC/MS," Journal of Pharmaceutical and Biomedical Analysis, vol. 26 (2001) pp. 155-161.
R. Hansel et al. "Zur Struktur Des Sillybins: Synthese Von Unsymmetrisch Substituierten 2.3-Trans-Benzdloxanen," Tetrahedron Letters, vol. 10 (1969), pp. 4417-4420.
David Y.-W. Lee et al. "Molecular Structure and Stereochemistry of Silybin A, Silybin B, Isosilybin A, and Isosilybin B, Isolated From *Silybum marianum* (Milk Thistle)," J. Nat. Prod. (2003) vol. 66, pp. 1171-1174, XP009121703.

(Continued)

*Primary Examiner* — Nizal Chandrakumar
(74) *Attorney, Agent, or Firm* — Miles & Stockbridge, P.C.

(57) ABSTRACT

The invention relates to a method for the preparation of amorphous silibinin (or its synonyms: silybin or silibin) derived from a milk thistle fruit extract having an increased release rate and improved absorbability or bioavailability, and to the use of amorphous silibinin for the treatment or prevention of liver diseases, preferably for the treatment of viral hepatitis, e.g. hepatitis B or C, in particular in a patient who will undergo or has undergone liver transplantation. Preferably, the amorphous silibinin is adapted for oral administration.

14 Claims, 16 Drawing Sheets

(56) References Cited

OTHER PUBLICATIONS

Nam-Cheol Kim et al. "Complete Isolation and Characterization of Silybins and Isosilybins From Milk Thistle (*Silybum marianum*)," Organic & Biomolecular Chemistry (2003) vol. 1, pp. 1684-1689.

Janiak Bernard "Phytochemisch-Pharmakognostische Untersuchungen der Fructus Cardui Mariae," Berlin University of Applied Sciences (1960) pp. 1-63.

K. H. Bauer et al., Lehrbuch der Pharmazeutischen Technologie [Textbook of Pharmaceutical Technology], WVG Stuttgart (1999) pp. 1-8.

H. P. Fiedler, Lexikon der Hilfstoffe für Pharmazie, Kosmetik und angrenzende Gebiete [Encyclopedia of excipients for pharmacy, cosmetics and related areas], Editio Cantor Aulendorf, 2001.

* cited by examiner

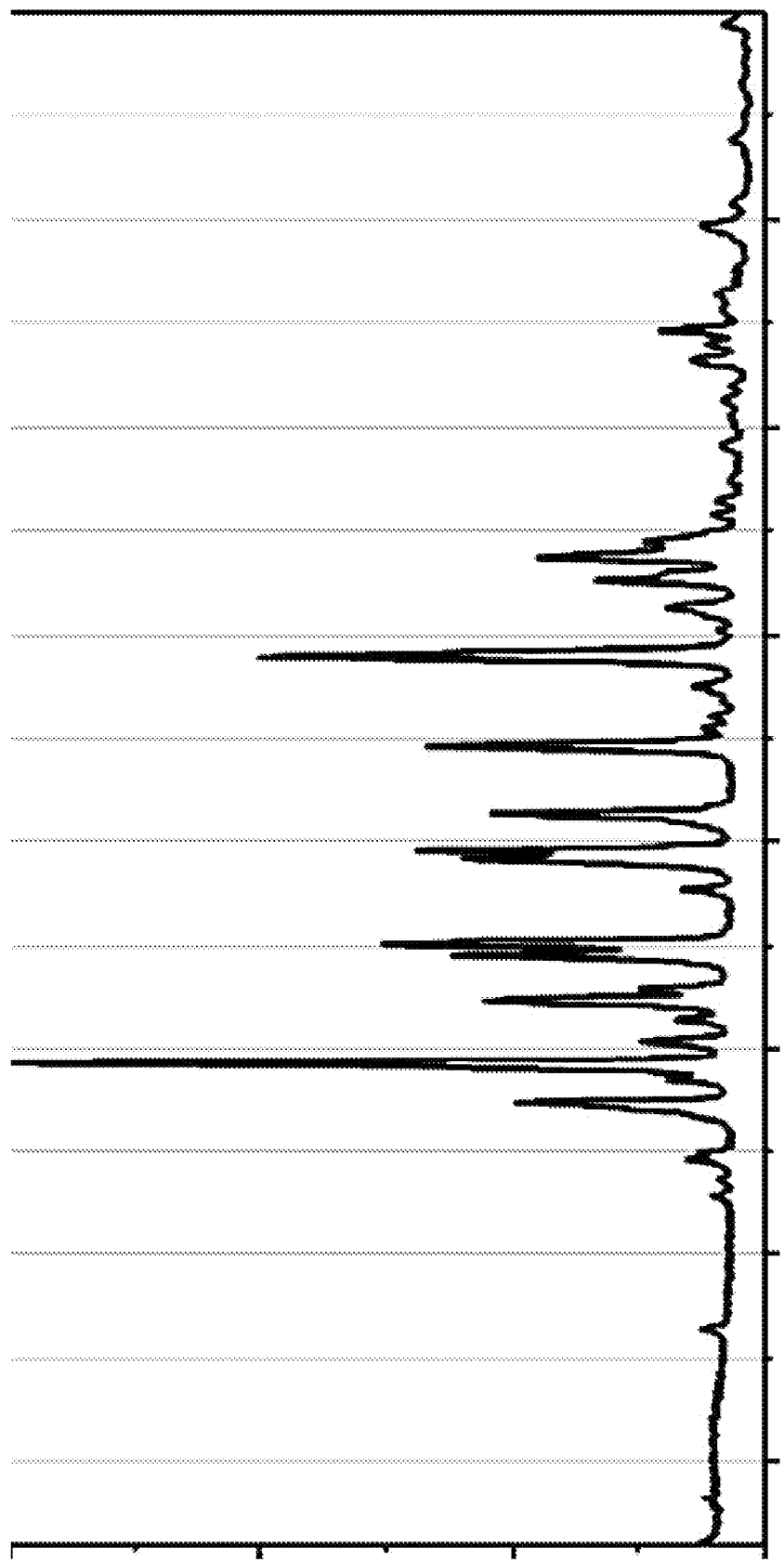

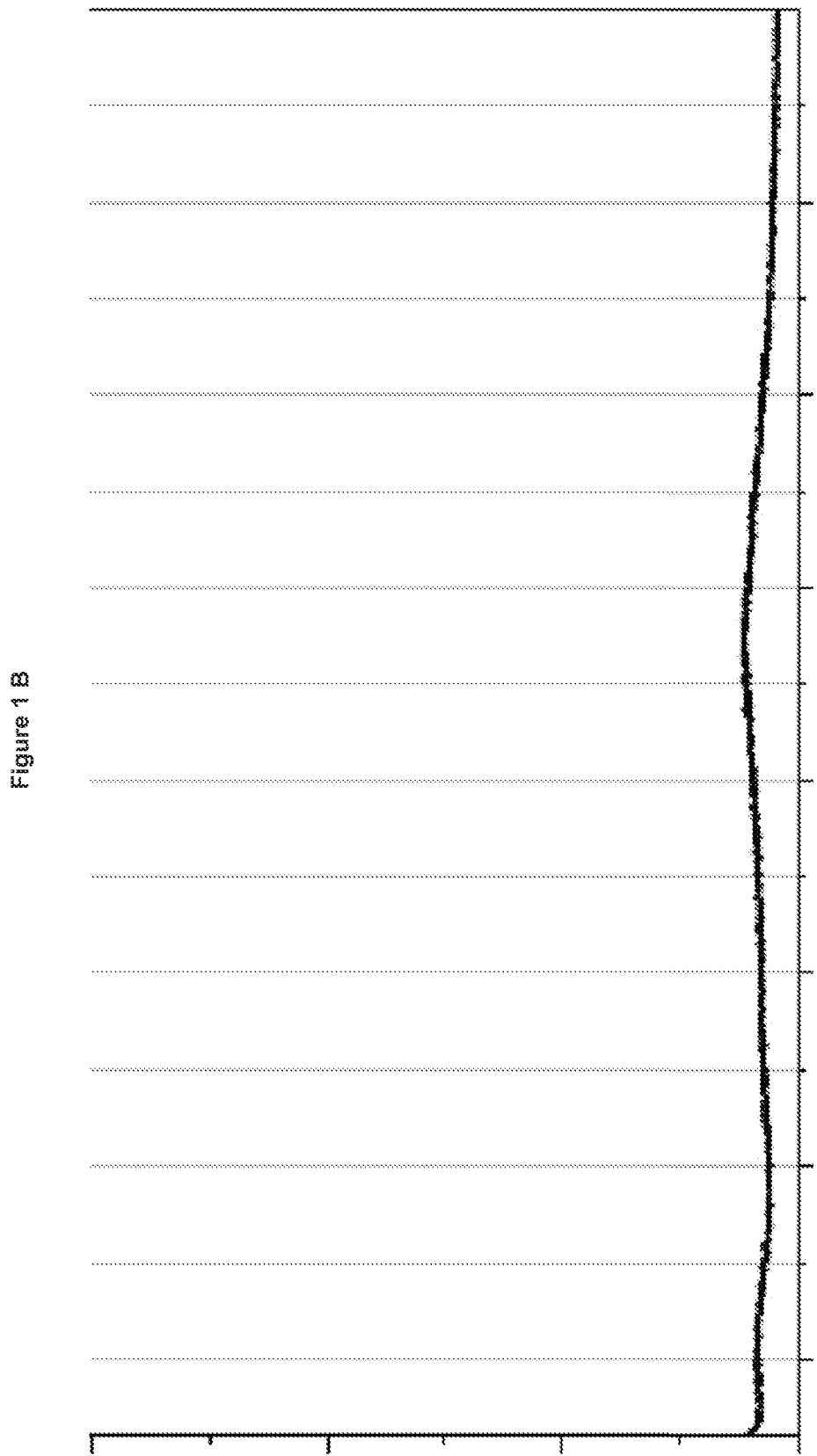

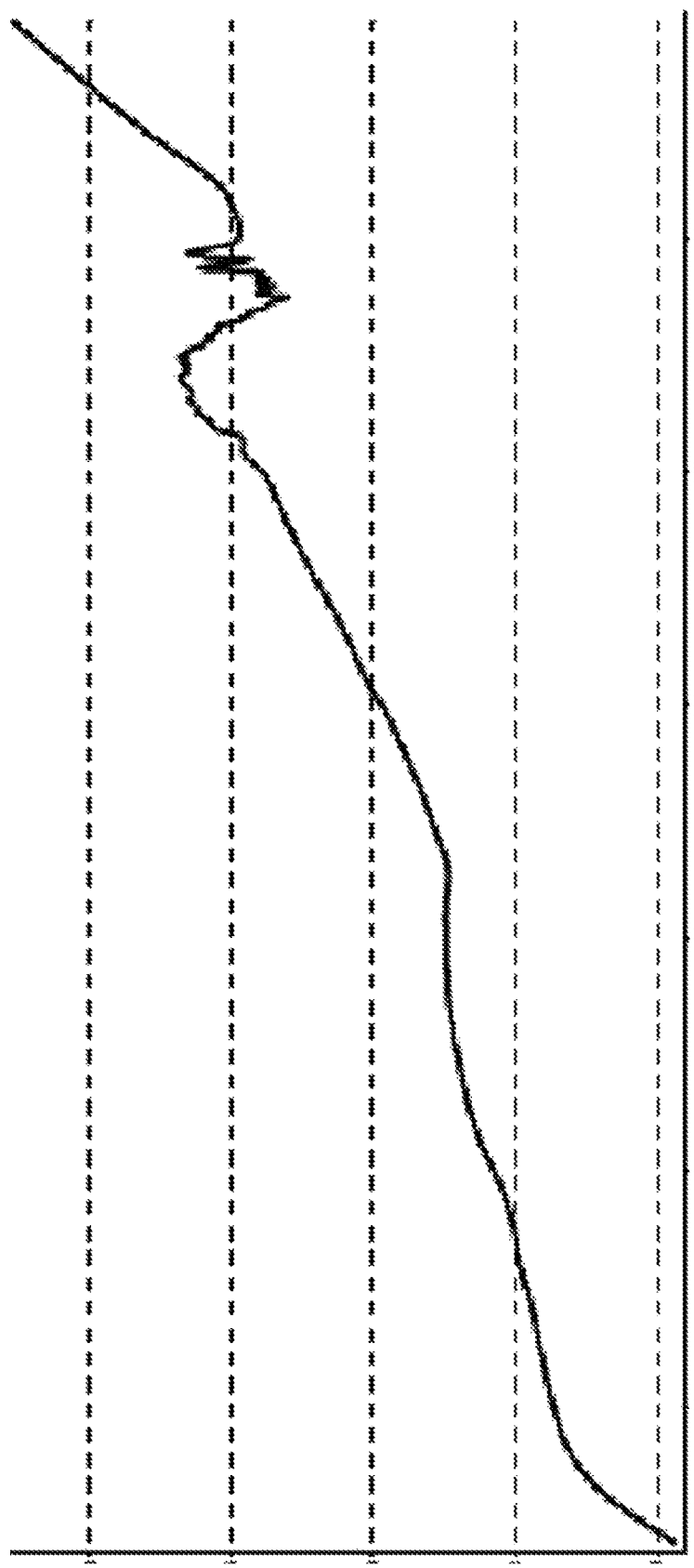

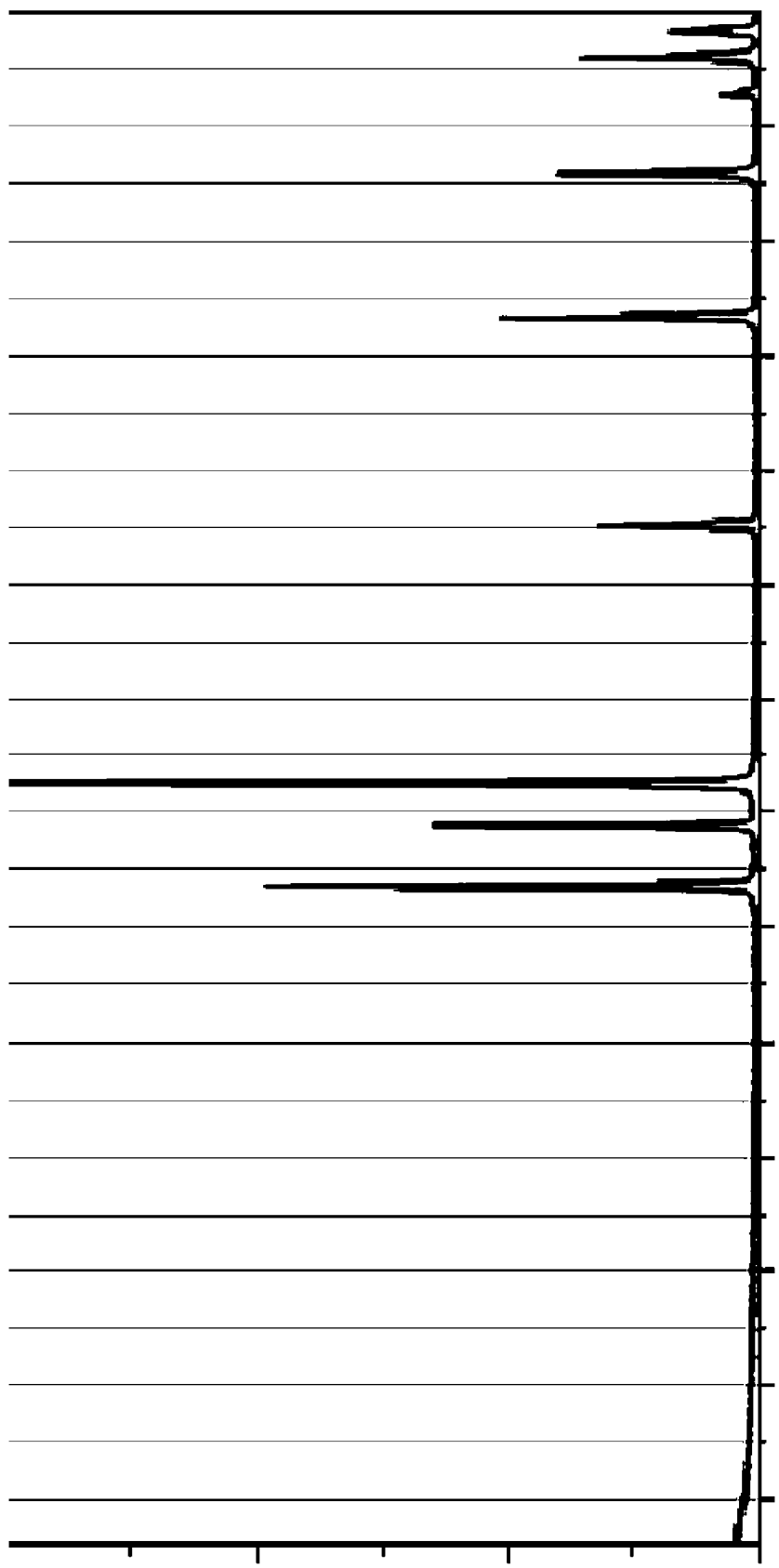

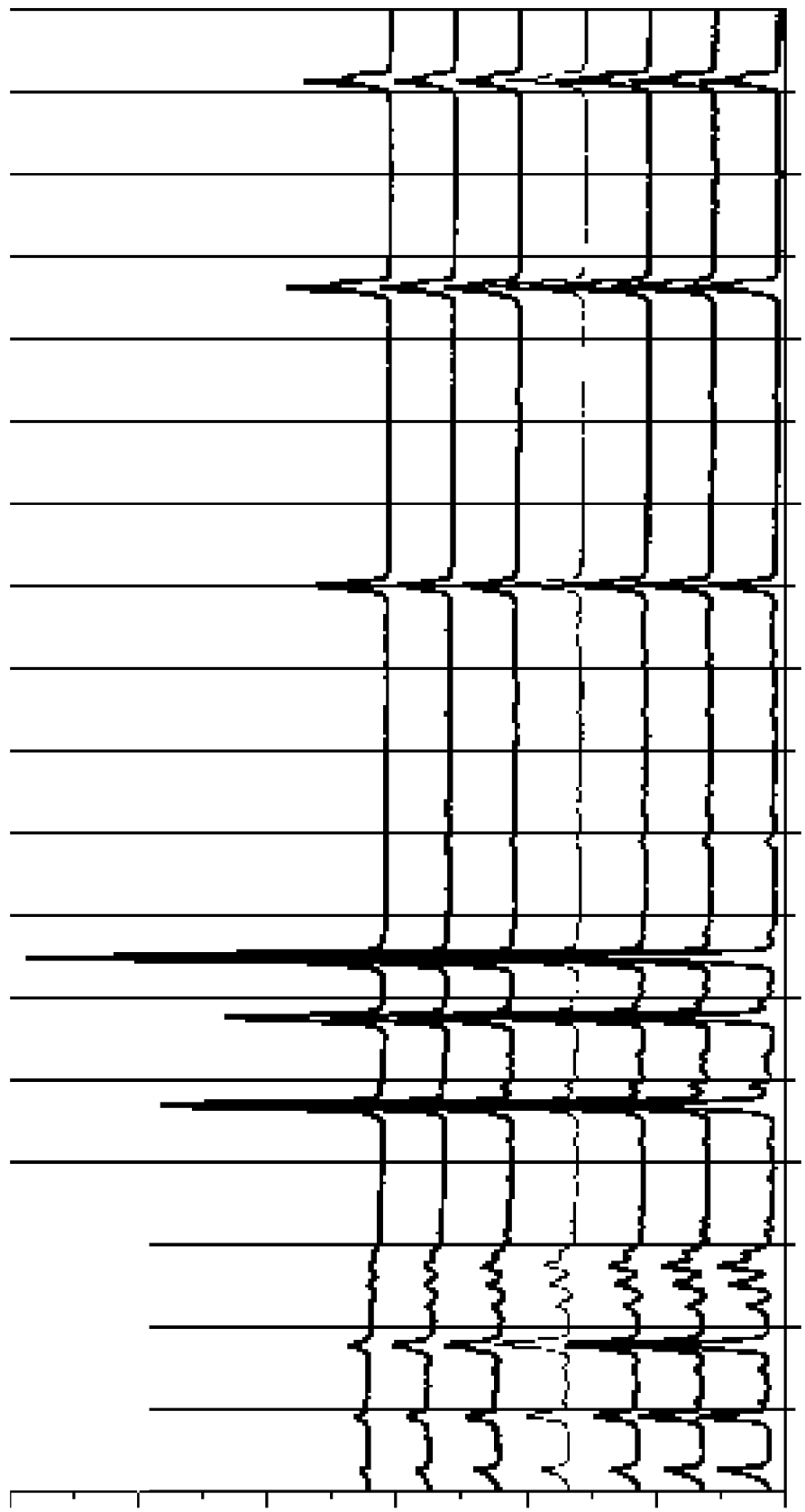

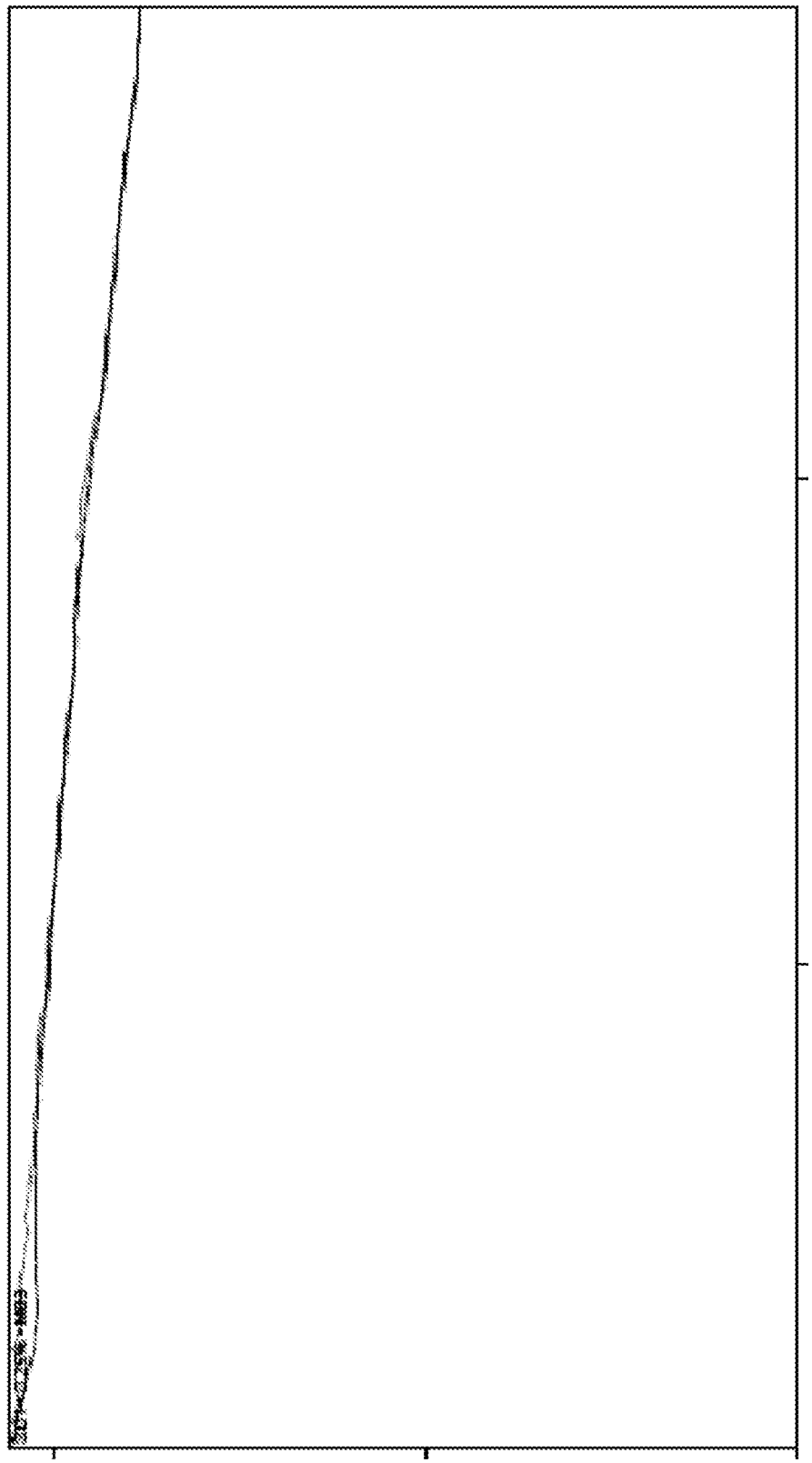

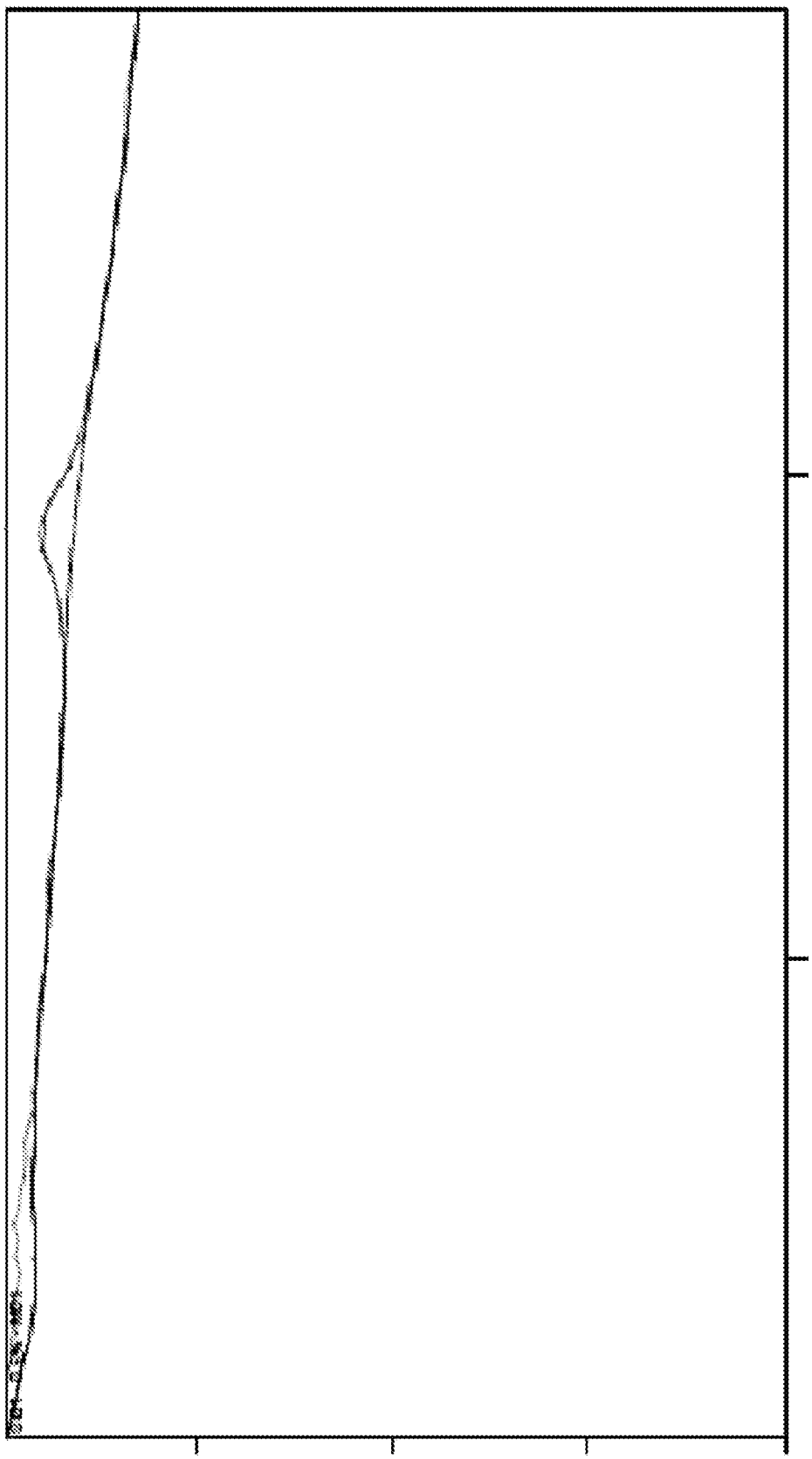

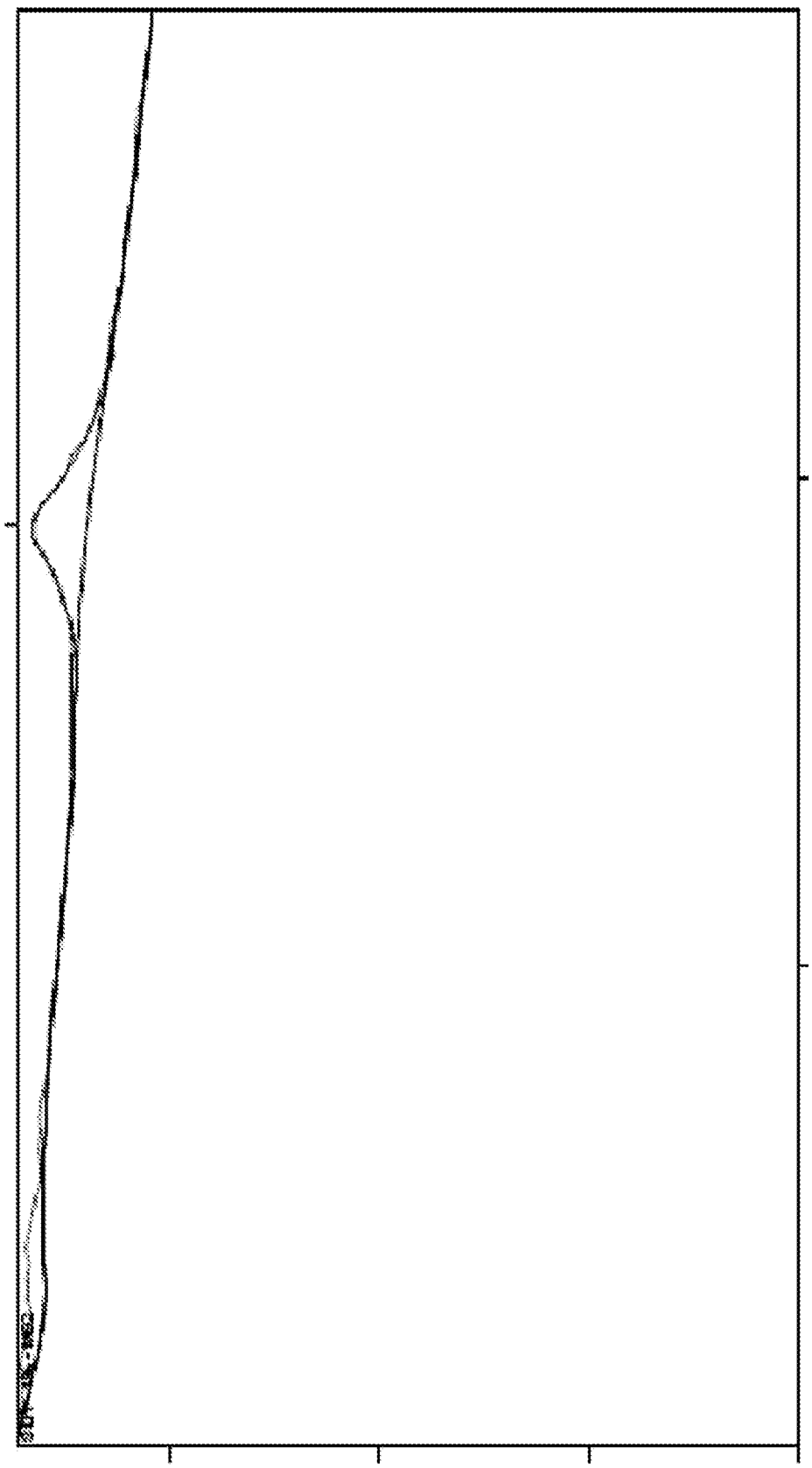

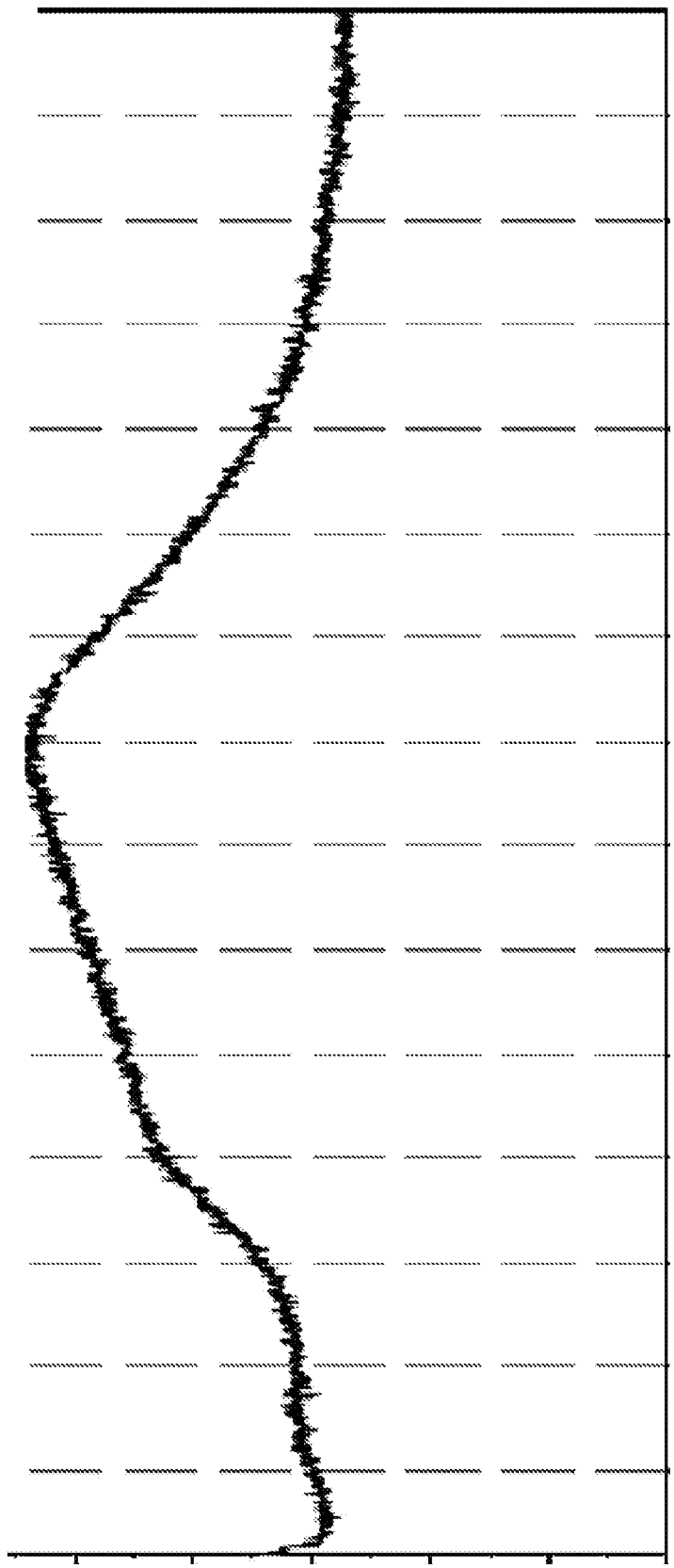

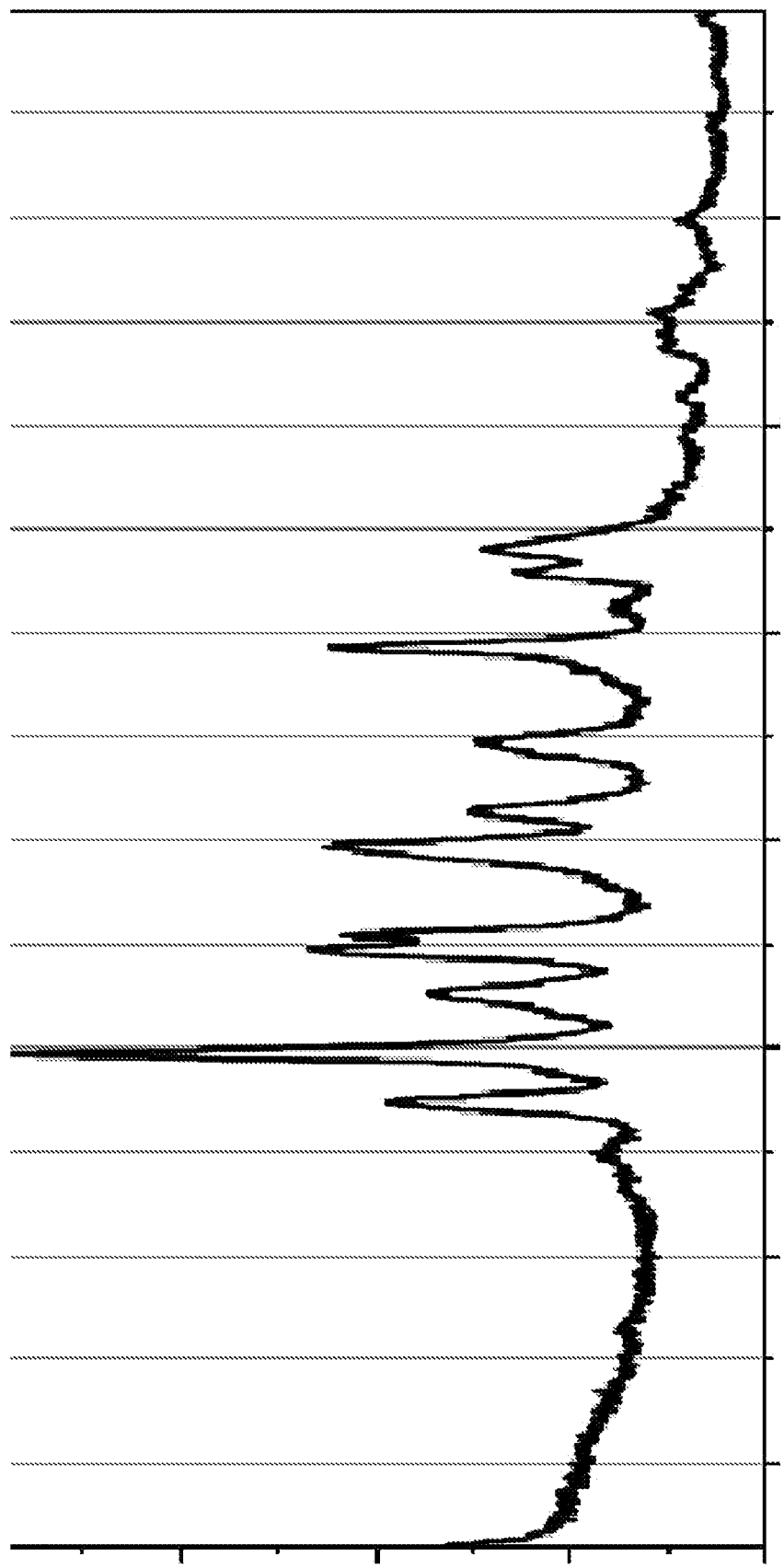

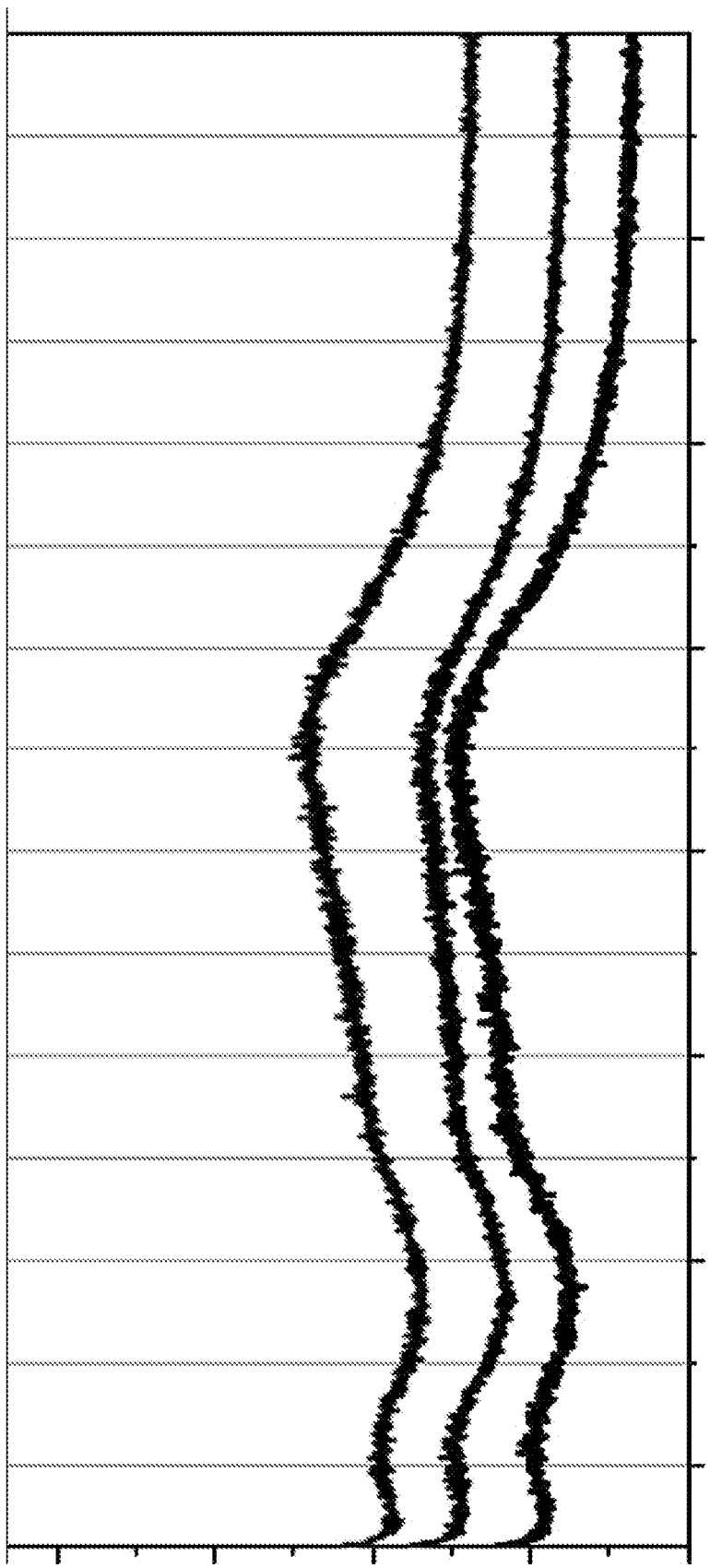

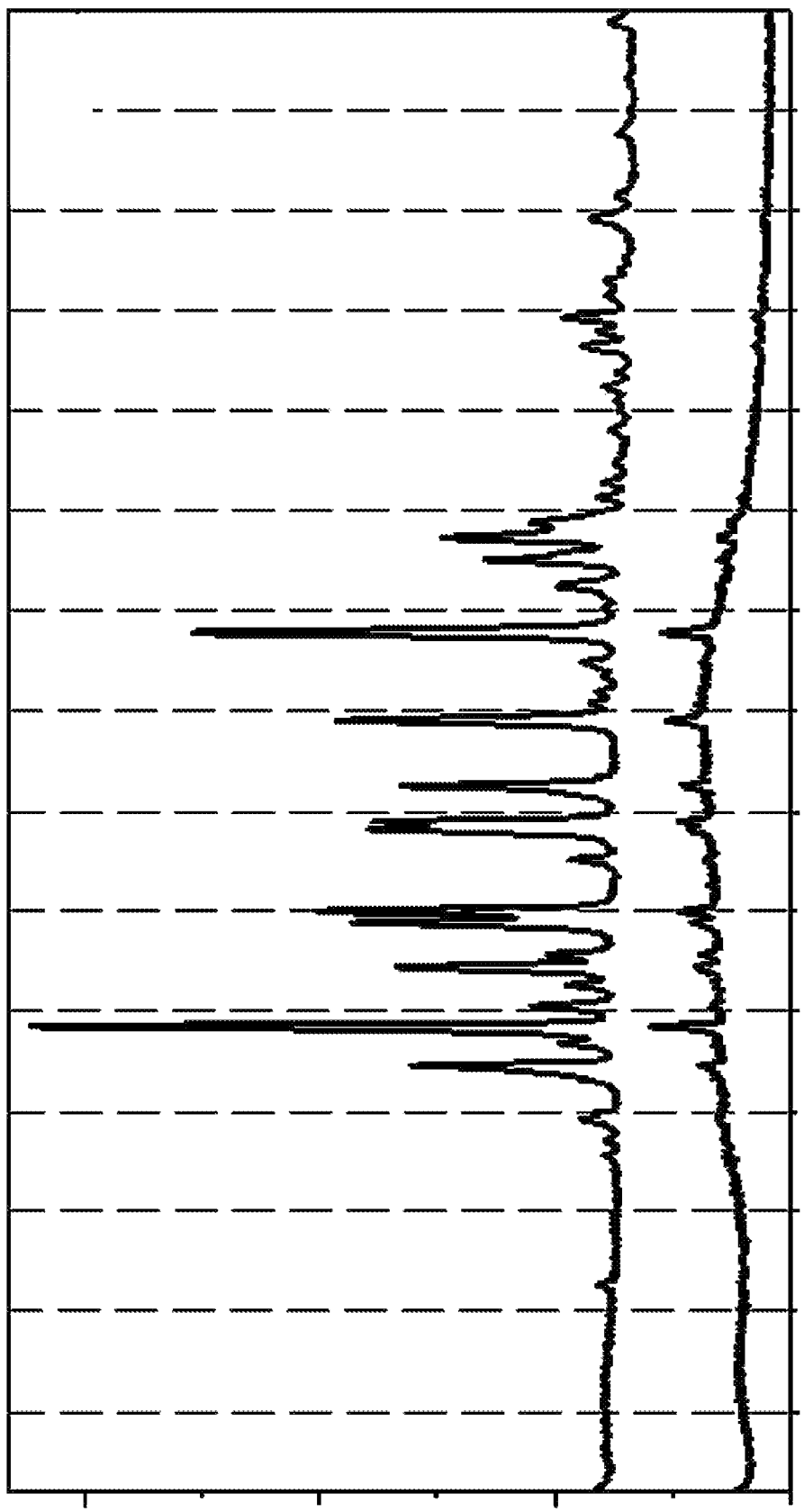

AMORPHOUS SILIBININ FOR THE TREATMENT OF VIRAL HEPATITIS

CROSS REFERENCE TO RELATED APPLICATIONS

This application is a §371 National Stage Application of PCT/EP2010/002978, filed May 14, 2010, which claims priority to EP09160322.5, filed May 14, 2009; EP09006663.0, filed May 18, 2009; and EP09006804.0, filed May 20, 2009.

BACKGROUND OF THE INVENTION

1. Field of the Invention

The invention relates to a method for the preparation of amorphous silibinin (or its synonyms: silybin or silibin) derived from a milk thistle fruit extract having an increased release rate and improved absorbability or bioavailability, and to the use of amorphous silibinin for the treatment or prevention of liver diseases, preferably for the treatment of viral hepatitis, e.g. hepatitis B or C, in particular in a patient who will undergo or has undergone liver transplantation. Preferably, the amorphous silibinin is adapted for oral administration.

2. Description of Related Art

The milk thistle (*Silybum marianum* or *Carduus marianus*) is a plant which is cultivated in particular in southwest and central Europe (Austria, Hungary), and which has become naturalized in Eurasia, North America, South America, and Australia. Production areas are also found in China.

Silymarin is contained in the dried ripe fruit of *Silybum marianum* (L.) *Gaertneri* (Fam. Asteraceaea) from which the pappus has been removed and which has a minimum silymarin content of 1.5% (*Pharmacopoea Europaea* (hereinafter: Ph. Eur.), 2007). Tinctures (usually alcoholic extracts) made from milk thistle have been known since ancient times. Isolated silymarin is particularly suitable (for example, DE 1 923 983, DE 1 767 666 (Madaus)). The efficacy of milk thistle (seeds or fruits) in the treatment and prevention of various forms of liver and gall bladder dysfunctions is known.

Silymarin is a complex of flavonolignans, i.e., polyhydroxyphenylchromanones, and was first isolated from the plant in the 1960s (Dissertation, Janiak Bernhard, June 1960, Berlin University of Applied Sciences (DE 2020407), Pelter A., Hansel R., Tetrahedron Letters, 25, 1968.

Silibinin {3,5,7-trihydroxy-2-(3-(3-hydroxy-4-methoxyphenyl)-2-(hydroxymethyl)-2,3-dihydro-benzo[b][1,4]-dioxin-6-yl)chroman-4-one; or according to Ph. Eur. (2R,3R)-3,5,7-trihydroxy-2-[(2R,3R)-3-(4-hydroxy-3-methoxyphenyl)-2-(hydroxymethyl)-2,3-dihydro-1,4-benzo-dioxin-6-yl]-2,3-dihydro-4H-1-benzopyran-4-one} is the main constituent of silymarin and the main flavonolignan extracted from milk thistle (*Silybum marianum Gaertneri*).

Silibinin has the following structure:

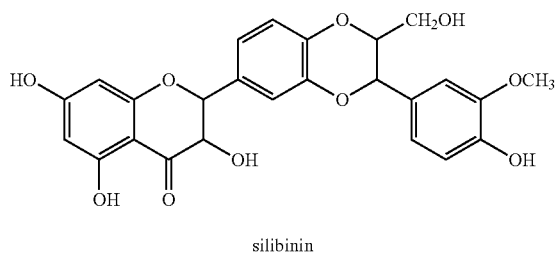 [SMILES: COc1cc(C2Oc3cc(C4Oc5cc(O)cc(O)c5C(=O)C4O)ccc3OC2CO)ccc1O]

silibinin

The diastereomers silibinin A and silibinin B are distinguished in the literature:

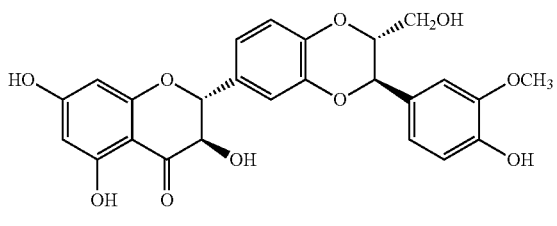

silibinin A

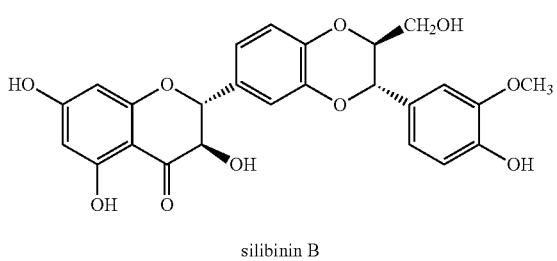

silibinin B

Silibinin, the main constituent of silymarin, is usually present in an about 50:50 mixture of Silybin A and Silybin B. Further constituents of silymarin include isosilibinin (isosilybin A and isosilybin B), silidianin (silydianin), silicristin (silycristin), isosilycristin, taxifolin and others, such as known secondary components including dehydrosilibin, 3-desoxysilicristin, desoxysilidianin (silymonin), silyadrin, silybinom, silyermin, and neosilymerin. The primary constituents are the four flavonolignans silibinin, silidianin, and silicristin as well as isosilibinin. In these flavonolignan structures, taxifolin is linked to conifery alcohol. Methods for isolating silibinin are known from the prior art (e.g., U.S. Pat. No. 4,871,763; D. Y.-W. Lee et al., J. Nat. Prod. 2003, 66, 1171-1174).

The fruits of the milk thistle are typically used for preparing the extract. Such extracts from milk thistle and methods for preparing them have previously been described in the prior art, for example as disclosed in DE 1 923 982, DE 29 14 330 (Madaus).

Also known is a dried extract of milk thistle fruit (Extr. cardui mariae fruct. siccum) which is obtained from the plant drug using, among others, the extraction agent ethyl acetate, and standardized in accordance with the applicable Ph. Eur.

The stated requirements for a dry extract are a content of preferably 30-65% by weight silymarin (other content ranges are possible), the silymarin portion containing the following fractions:

40-65% by weight: Silibinin A and B (diastereomeric mixture, $C_{25}H_{22}OH_{10}M_w$ 482.4) and 10-20% by weight: Isosilibinin A and B (diastereomeric mixture, $C_{25}H_{22}OH_{10}M_w$ 482.4) and 20-45% by weight: Silidanin and silicristin ($C_{25}H_{22}OH_{10}M_w$ 482.4).

For preparation of an extract, the raw material (in this case, the plant drug) is usually degreased, extracted, filtered, concentrated, and purified. For said continuous extraction, using ethyl acetate/ethanol/acetone/methanol (optionally in aqueous form) or aqueous mixtures with the above-referenced solvents, filtration is usually performed, followed by concentration. Purification is then carried out using ethanol and hexane (further degreasing), thus obtaining the above-referenced content of silymarin. Such a composition allows a silymarin release rate of 30% to approximately 40% (measured in accordance with Ph. Eur. 5.7; 2.9.3 (01/2006:20903 as amended, for example using the basket or paddle method)).

However, there is a great need for increasing the release rate of silymarin, preferably silibinin, in the native extract.

Silibinin is lipophilic and thus, has a very poor solubility in aqueous liquids. It is known that flavonolignans, particularly silibinin, have little or no solubility in water (the solubility of pure silymarin is approximately 0.08 g/l at pH 6.9). Because of this solubility characteristic the release rate of flavonolignans, particularly silibinin, and de facto their bioavailability or absorbability in the body of humans or mammals, is inadequate.

In order to increase the release rate, attempts have been made to derivatize the flavonolignans, using polyalcohols, amino sugars, or esters, for example, or to complex them using inclusion compounds such as cyclodextrin (EP 0 422 497 B1 (Madaus)), or using complexing compounds, for example phosphatidylcholine. Such complexes, however, are not satisfactory in every respect and there is a need for medicaments that contain silibinin without requiring the presence of solubilizing complexes, such as phopholipid complexes or cyclodextrin inclusion complexes, and at the same time, providing a sufficient bioavailability of silibinin so that comparatively high plasma levels that are required for the treatment of viral hepatitis can be achieved upon oral administration.

It is also known from the prior art that the release rate may be increased by use of carrier substances such as 1-vinyl-2-pyrrolidone, mannitol, and others (EP 0 722 918 B1, U.S. Pat. No. 5,906,991 (Madaus)). In addition, wetting agents such as polysorbates (tensids) are necessary. EP 1 021 198 B1 (Madaus) discloses a silymarin coprecipitate with the use of PEG. Polar silibinin-esters are commercially available as an infusion solution, for example, under the name Legalon® SIL in the Federal Republic of Germany.

However, these referenced methods all have the disadvantage that dosing is made more difficult, and foreign substances may arise which may have imprecisely defined side effects.

L. Yu, Advanced Drug Delivery Reviews, 2001, 48, 27-42 relates to amorphous pharmaceutical solids, their preparation, characterization and stabilization.

WO 2009/080006 relates to a method for producing a milk thistle extract, particularly a flavonolignan preparation, having an increased release rate and improved resorbability, and to the use thereof, particularly for the therapy and prophylaxis of liver diseases.

U.S. Pat. No. 4,871,763 provides a process for the preparation of substantially pure silibinin from the fruits of *Silybum marianum*, as well as pharmaceutical compositions containing it for the treatment of diseases of the liver.

GB 2 167 414 discloses silibinin derivatives useful in pharmaceutical compositions for treating burn damage, liver damage or fungal poisoning.

SUMMARY

It is an object of the present invention to provide a silibinin having an improved bioavailability.

Further, there is a need for medicaments, particularly adapted for oral administration, for the treatment of viral hepatitis, in particular of hepatitis B and C. The medicament should provide the lipophilic drug silibinin with sufficiently high bioavailability without requiring the presence of solubilizing complexes, such as phopholipid or cyclodextrin inclusion complexes.

Thus, it is also an object of the invention to make available a medicament, in particular for oral administration, for the treatment of viral hepatitis, in particular of hepatitis B or C, which has advantages compared to the medicaments of the prior art. The medicament should if possible have no or only slight side effects and be effective, e.g., in hepatitis C patients who do not sufficiently respond to conventional combination therapy with PEG interferon/ribavirin, and/or in (formerly) hepatitis C patients who will undergo or have undergone liver transplantation. Further, the medicament should have pronounced antiviral properties at high bioavailability and thus lastingly decrease the virus load. Still further, the medicament should render the highly lipophilic silibinin bioavailable in comparatively high dosages without requiring the presence of solubilizing complexes, such as phopholipid or cyclodextrin inclusion complexes.

This object is achieved by the subject matter of the patent claims.

A first aspect of the invention relates to a process in order to obtain silibinin, due to the fact, that silibinin is the therapeutically most active compound in the mixture of any milk thistle extract.

The object is solved by the following process in order to obtain and/or enrich amorphous silibinin comprising the steps:

A.) the plant drug, i.e. the silibinin contained in the naturally occurring plant and seeds, respectively, is extracted with a solvent having moderate polarity (preferably having a dipole moment of less than 2 Debye, e.g. ethyl acetate, ethanol, methanol, optionally containing aqueous fractions), preferably at 40-80° C., particularly preferably 50-70° C., B.) separated, preferably filtered, C.) concentrated, preferably under vacuum with stirring, at a temperature less than 60° C., preferably less than 40° C., and optionally washed with hot water, D.) combined with ethanol or a solvent of similar polarity, preferably a protic solvent, preferably having a dipole moment of less than 2, preferably adjusted to a water content of 130-180 g/l and then combined with hexane or a solvent of similar polarity and concentrated, preferably under vacuum, and the hexane phase is removed, E.) concentrated, preferably less than 65° C., F.) separated, preferably filtered, G.) the solid phase is combined with ethanol or a solvent of similar polarity, preferably a protic solvent, preferably having a dipole moment of less than 2, preferably adjusted to a water content of 130-180 g/l, H.) at least one adsorbent is added, preferably activated charcoal, I.) separated, preferably filtered, preferably less than 80° C., more preferably 50-60° C. and concentrated and crystallized, J.) separated, preferably filtered, and if required steps G, I, J.) are repeated in order to enrich silibinin with a content of more than 95% weight, K.) optional, filtration, washing, drying, preferably under vacuum and, if required, repeating these steps; and optionally comminuted, L.) combined with anhydrous alcohol, preferably ethanol, preferably adjusted to a concentration of 2 to 12 wt.-% with respect to dry material, optional stirred, refluxed, cooled and filtered;

M.) dried, optionally comminuted, milled, post-dried and homogenized;

a) feeded to an atmosphere dryer (spray dryer) at an inlet temperature of preferably from 180° C. to 200° C. and an outlet temperature of preferably from 80° C. to 120° C., to obtain a dry powder with ethanol content preferably around 5% and water content preferably lower than 1%; or b) concentrated to maximum 20% of dry residue and then dried directly in the reactor, preferably at less than 80° C., more preferably at 50-60° C. under vacuum to obtain a dry powder;

The dried product is preferably post dried, if necessary at maximum 80° C. and maximum 40 mbar of pressure.

Surprisingly, step L.) results in a significant increase in the silibinin release rate (solubility), due to the fact, that a novel amorphous silibinin is obtained. This is particularly advantageous, since a lower dosage of silibinin, if isolated or enriched, according to the invention is achieved and the bioavailability or absorbability is increased. It is also advantageous that a quality is attained which in the prior art is achievable only using additives, supplements, carrier substances, and wetting agents.

It has been surprisingly found that the degree of amorphicity of silibinin that is obtainable by the method of the invention is very high, typically well above 90 wt.-%. This is of particular advantage, as if the amorphous purity is lower than 90% (i.e. the content of crystalline silibinin higher than 10%), the stability of the amorphous state is compromised, since it tends to crystallize in the short term. Shelf life would be decreased, because if the amorphous silibinin crystallizes upon storage, the crystalline material would not be soluble anymore and thus, would lack bioavailability. Preliminary tests concerning the minimum content of crystalline silibinin that challenge product stability revealed values within the range of from about 10 to about 20%, depending upon the relative humidity.

BRIEF DESCRIPTION OF THE DRAWINGS

The Figures attached to the application show the following:
FIG. 1 A: Crystalline silibinin standard
FIG. 1 B: Amorphous silibinin standard
FIG. 2 A: DSC of crystalline silibinin standard
FIG. 2 B: DSC of amorphous silibinin standard
FIG. 2 C: DSC of mixtures of: 10, 25, 35, 50, 60, 75, and 100% of crystalline silibinin standard in amorphous silibinin standard.
FIG. 6: XRPD spectrum for a representative lot of amorphous silibinin
FIG. 7: XRPD spectrum for a representative lot of silibinin obtained according to the process without steps L and M:
FIG. 8 A: XRPD spectra of pure amorphous silibinin after storage at 4, 25, and 40° C. for 2 months.
FIG. 8 B: XRPD spectra of 10% crystalline-amorphous silibinin mixture at the starting time and after storage at 25° C. for 2 months

DETAILED DESCRIPTION OF A PREFERRED EMBODIMENT

Figure 2:
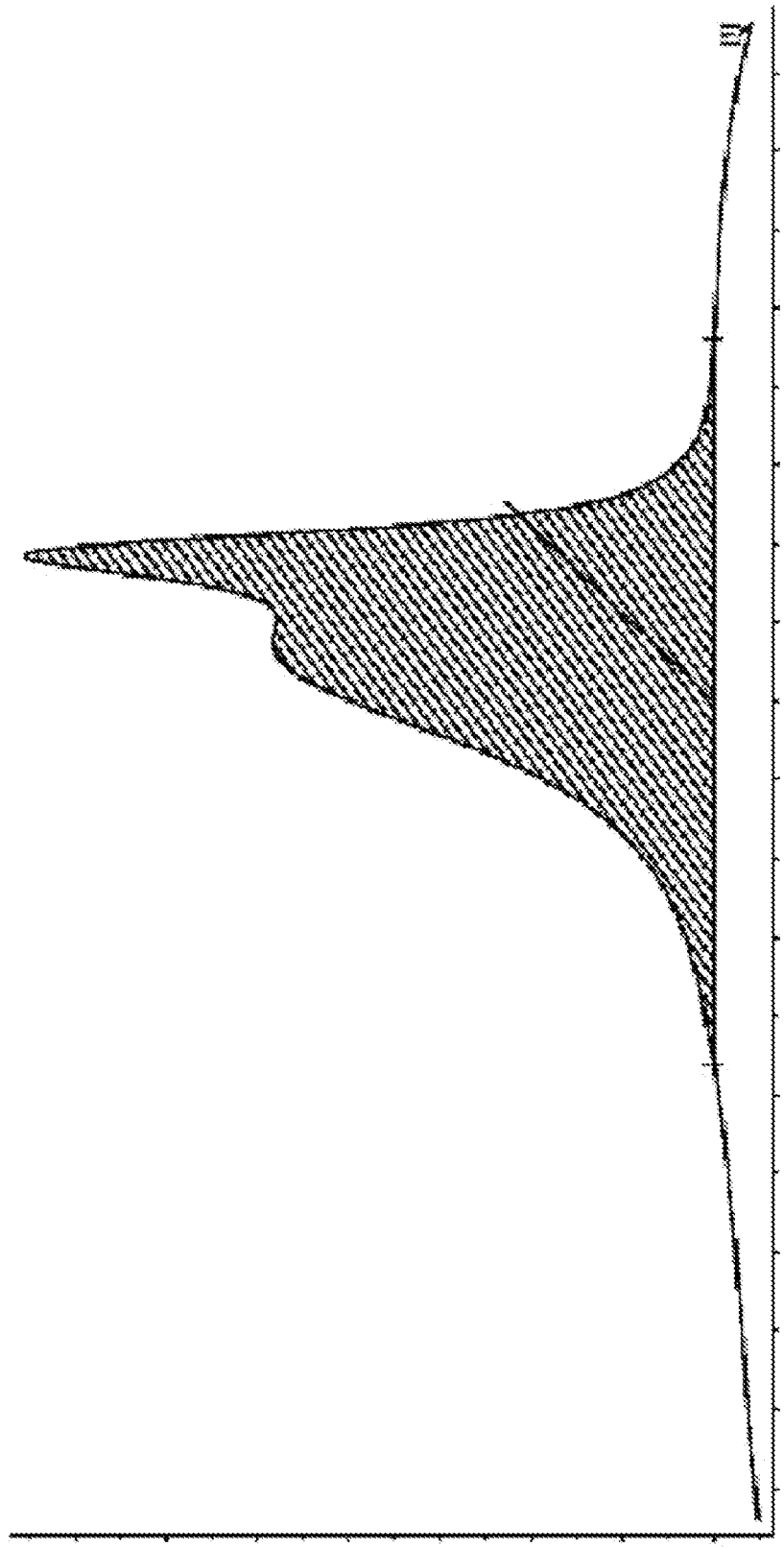
Figure 2:
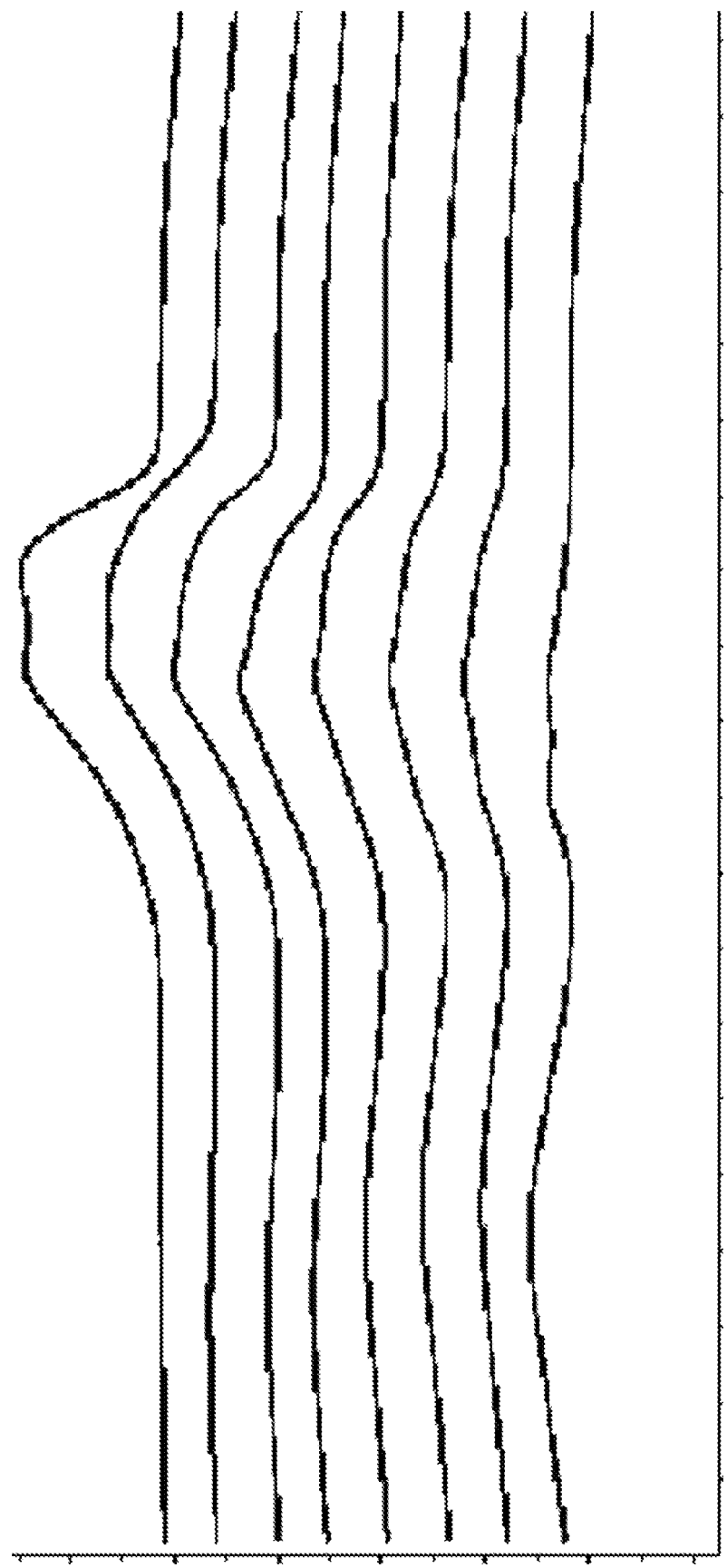

The invention relates to a novel amorphous silibinin as such and obtainable or derived from a milk-thistle extract.

In step A.) of the method according to the invention, silibinin is extracted with a solvent having moderate polarity (e.g. ethyl acetate, ethanol, methanol, optionally containing aqueous fractions), preferably at 40-80° C., particularly preferably 50-70° C.

The starting material is preferably milk thistle or a part thereof, e.g. the fruits. A skilled person knows that it may be helpful to comminute the starting material prior to extraction to facilitate and accelerate the release of silibinin. Thus, prior to extraction, the starting material, preferably milk thistle fruits, are preferably pretreated, preferably mechanically pre-degreased. Preferably, the milk thistle fruits are mechanically separated from foreign materials and metallic parts, e.g. by sieving through a 1 cm sieve and afterwards using a magnetic separator. The milk thistle fruits are then preferably milled, e.g. by means of a mill containing a plurality of rollers. Crushing and pressing is preferably performed at ambient temperature and a pressure of at least 50 bar, e.g. 65 bar. Thereafter, the partially degreased milk thistle fruits are preferably warmed on a screw conveyor to a temperature of 40-50° C. The yield of this preferred method step is variable and depends upon the kind and the oil content of the fruits.

Subsequently, the preferably pre-degreased drug (silibinin) is preferably introduced into percolators and is extracted with the solvent having moderate polarity, preferably ethyl acetate, preferably at an entrance temperature of 62° C. and 66° C. The extraction is preferably performed in a continuous fashion. Upon extraction, the water contained in the milk thistle fruits enriches with the time the water content of the extraction solvent ethyl acetate. Preferably, the maximum water content shall not exceed 35 g/l and if necessary, an adjustment with ethyl acetate can be carried out. The water contents can be determined by Karl Fischer titration (Method: Ph. Eur. 2.5.32—Water micro determination).

Step A.) typically does not yield pure silibinin but rather a complex mixture of constituents originally contained in the starting material including silibinin. Said complex mixture, i.e., the intermediate product obtained in step A.) is then subsequently subjected to step B.). Step A.) typically yields a heterogeneous system comprising the starting material and the solvent whereas some constituents of the starting material among which silibinin have been dissolved, at least partially, in the solvent (extract).

In step B.) of the method according to the invention, the intermediate product obtained in step A.) is separated, preferably from the solids, preferably by filtration. In other words, in step B.) the liquid phase is separated from the solid residue. In order to eliminate residual drug particles, the obtained miscella are preferably filtered through a GAF filter (25-50 μm). The obtained miscella is preferably transparent (visual control). The liquid phase, i.e. the extract, is subsequently subjected to step C.).

In step C.) of the method according to the invention, the intermediate product obtained in step B.) is concentrated, preferably under vacuum with stirring, at a temperature less than 60° C., preferably less than 40° C., and optionally washed with hot water. In a preferred embodiment, the entire or nearly the entire solvent is removed upon concentration. In order to eliminate as much as possible the ethyl acetate, the water-soluble impurities and the milk thistle oil, the pre-concentrate is preferably concentrated under vacuum with stirring at a temperature ≤40° C. in a recipient with water. The phases which are formed in the reactor are preferably separated by decanting. When washing with hot water is performed, this can be done e.g. on a filter or a glass frit. Washing may be performed in order to remove water solubles from the remainder. The precipitate is preferably washed with an excess of hot water. The water temperature at the entrance is preferably 70-80° C. The exceeding water is preferably aspirated.

In step D.) of the method according to the invention, the intermediate product obtained in step C.), i.e. the washed residue, is combined with ethanol or a solvent of similar polarity, preferably adjusted to a water content of 130-180 g/l and then combined with hexane or a solvent of similar polarity and concentrated, preferably under vacuum, and the hexane phase is removed.

In the first step, a solution preferably having 8-100 g/l of dry residue is prepared dissolving the resulting cake in ethanol or a solvent of similar polarity according to the solubility of the content (preferred water content 130-180 g/l). Then it is preferably warmed up to reflux. As soon as the solution is obtained, it is preferably cooled down to <30° C. The solution is preferably adjusted with water or solvent (e.g. ethanol) in order to reach the desired water content (Karl Fischer titration, Method: Ph. Eur. 2.5.32—Water micro determination).

In the second step, the solvent solution (e.g. ethanol solution) is preferably degreased with hexane. Therefore, the ethanol solution is preferably first saturated with hexane and afterwards, in order to eliminate the not dissolved components, it is preferably centrifuged through a chamber separator and filtered through a plate filter. The degreasing is preferably carried out in a counter-current partition column with hexane. The ethanol solution is preferably filtered through a 5 µm bag filter. Hexane is preferably distilled off from the hexane phase. The oily residue is preferably discarded.

In step E.) of the method according to the invention, the intermediate product obtained in step D.) is concentrated, preferably at a temperature of less than 65° C. Preferably, the filtered ethanol phase is concentrated in a reactor at a maximum temperature of 65° C. under vacuum and with stirring until a 35-45% of dry residue is obtained.

In step F.) of the method according to the invention, the intermediate product obtained in step E.) is separated, preferably filtered. Preferably, the concentrate is filtered through a membrane press filter. There are two phases: the paste filtrate and liquid. The paste is used in the following steps.

In step G.) of the method according to the invention, the intermediate product obtained in step F.), i.e. the solid phase (paste), is combined with ethanol or a solvent of similar polarity, preferably adjusted to a water content of 130-180 g/l. Preferably, a solution having 5-10 g/l of dry residue is prepared by dissolving the paste in ethanol (water content 130-180 g/l).

In step H.) of the method according to the invention, at least one adsorbent is added to the intermediate product obtained in step G.), preferably activated charcoal. Preferably, after dissolving the paste, approx. 2% of activated charcoal, calculated on dried substance, is added to this solution and the liquid is refluxed, in order to achieve a good mixing.

In step I.) of the method according to the invention, the intermediate product obtained in step H.) is separated, preferably filtered, preferably less than 80° C., more preferably 50-60° C. and concentrated and crystallized. Preferably, the product is filtered at temperature between 50-60° C. through a plate filter and goes to the concentration. Preferably, the concentrating temperature is ≤65° C. under vacuum until a dry residue of 35-45% is obtained and afterwards the concentrate is preferably cooled down to ≤3° C. and preferably crystallized.

In step J.) of the method according to the invention, the intermediate product obtained in step I.) is separated, preferably filtered, and if required steps G, I, J.) are repeated in order to enrich silibinin with a content of more than 95% weight. Preferably, after cooling the product, it passes through a membrane press filter, in order to separate the solid from the residual liquid. Then a sample can be taken to determine the content of silibinin. If this content is <95% and the sum of isosilibinin, silidianin and silicristin is >1%, the process preferably goes back to the point G.) without adding activated charcoal, until a content of silibinin ≥95% is obtained and a sum of isosilibinin, silidianin and silicristin ≤1%. Determination can be carried out using a reversed-phase liquid chromatographic method in accordance with the Ph. Eur.

In step K.) of the method according to the invention, the intermediate product obtained in step J.) is optional, filtration, washing, drying, preferably under vacuum and, if required, repeating these steps and comminuted. Preferably, the substance is washed with cold water. Preferably, the drying of the product is achieved in a vacuum dryer preferably under a pressure from 70 to 1 mbar and at maximum temperature of the dryer jacket 80° C. The dried extract is preferably pre-crushed through a 1 mm sieve.

In step L.) of the method according to the invention, the intermediate product obtained in step K.) is combined with anhydrous alcohol, preferably ethanol, optional stirred, refluxed, cooled and concentrated, preferably less than 80° C., more preferably 50-60° C. under vacuum. Preferably, the pre-crushed silibinin is dissolved in ethanol ≥99.5% (V/V) until a 2%-10% of dry residue is obtained. The solution is preferably warmed up to reflux in a reactor provided with stirring and is immediately cooled down to preferably about 40° C. Following the cooling, the product is preferably filtered through a plate filter and introduced slowly into another reactor, where it is preferably concentrated at ≤65° C. under vacuum and with stirring until a syrup-like concentrate is obtained.

In a preferred embodiment, step L.) is conducted until the residual water/ethanol content is not more than 25 wt.-%, 22.5 wt.-%, 20 wt.-%, 17.5 wt.-%, 15 wt.-%, or not more than 12.5 wt.-%. In another preferred embodiment, step L.) is conducted until the residual water/ethanol content is not more than 10 wt.-%, 9.5 wt.-%, 9.0 wt.-%, 8.5 wt.-%, 8.0 wt.-%, 7.5 wt.-%, 7.0 wt.-%, 6.5 wt.-%, 6.0 wt.-%, 5.5 wt.-%, 5.0 wt.-%, 4.5 wt.-%, 4.0 wt.-%, 3.5 wt.-%, 3.0 wt.-% or not more than 2.5 wt.-%. In still another preferred embodiment, step L.) is conducted until the residual water/ethanol content is not more than 2.4 wt.-%, 2.3 wt.-%, 2.2 wt.-%, 2.1 wt.-%, 2.0 wt.-%, 1.9 wt.-%, 1.8 wt.-%, 1.7 wt.-%, 1.6 wt.-%, 1.5 wt.-%, 1.4 wt.-%, 1.3 wt.-%, 1.2 wt.-%, 1.1 wt.-%, 1.0 wt.-%, 0.9 wt.-%, 0.8 wt.-%, 0.7 wt.-%, 0.6 wt.-%, 0.5 wt.-%, 0.4 wt.-%, 0.3 wt.-%, 0.2 wt.-% or not more than 0.1 wt.-%.

In step M.) of the method according to the invention, the intermediate product obtained in step L.) is dried, optionally comminuted, milled, homogenized. Preferably, the final drying of the substance is carried out in a vacuum dryer, preferably at 70 to 1 mbar (temperature of the dryer jacket preferably ≤80° C.) or spray dryer (e.g. inlet temperature=200° C., outlet temperature 100-150° C.). The dried extract is preferably pre-crushed through 2 mm sieve. Thereafter, the product is preferably ground in a pin mill, provided with nitrogen, to get a fine powder. Finally, the milled product is preferably mixed in a cone, e.g. for 2 h.

In order to enrich or isolate amorphous silibinin the steps G., I., J.) can be repeated, wherein silibinin is enriched/obtained or isolated with a content of more than 95% (weight), preferably 100% (weight), preferably by means of one or more adsorbents (see step H.), e.g. activated charcoal or the like), hereinafter "silibinin according to the invention".

Hence, the invention relates to a novel amorphous silibinin having a purity of more than 95% (weight), more than 99% (weight), more than 99.5% (weight), 99.9% (weight) and 100%. The invention relates to an amorphous silibinin, which is substantially free of other silymarin components.

In a further preferred embodiment, the invention relates to a novel amorphous silibinin comprising essentially of an amorphous modification, wherein the non-amorphous or crystalline fraction is less than 20%, preferably less than 10%, particularly preferably less than 7%, even 5% or less.

Furthermore, the invention further relates to a purified amorphous silibinin, preferably having a silibinin release rate of 80% or greater, e.g. at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%; preferably being obtainable from an extract having a silymarin content of 15-85% by weight, in particular 30-65% by weight, and other silymarin components, as above mentioned are removed due to the inventive process.

The term "anhydrous alcohol" in step L.) preferably includes $C_1$-$C_4$ alcohols, particularly preferably ethanol, such as 99% or even 99.5% pure.

Within the scope of the present invention, "silymarin" refers to a substance mixture containing (at least) the four substances silibinin, silidianin, silicristin, and isosilbinin various concentrations. The ratios of these substances with respect to one another, and the presence of additional substances in the mixture, are not important. However, it is preferred that these substances meet the requirements of Ph. Eur.

A "silibinin release rate of 80% or greater" means that the amorphous silibinin is at least 80% soluble in aqueous solution (standard according to Ph. Eur.).

This advantageously results in improved absorbability and bioavailability.

A further aspect of the invention relates to amorphous silibinin that is obtainable by the method according to the invention. In a preferred embodiment, this is the amorphous silibinin that is contained in the pharmaceutical composition according to the invention and the pharmaceutical dosage form according to the invention, respectively.

Preferably, the amorphous silibinin that is obtainable by the method according to the invention has a degree of amorphicity of at least 95 wt.-%, more preferably at least 96 wt.-%, still more preferably at least 97 wt.-%, most preferably at least 98 wt.-% and in particular at least 99 wt.-%. In other words, the amorphous product that is obtainable by the method according to the invention preferably has a content of crystalline silibinin amounting to at most 5 wt.-%, more preferably at most 4 wt.-%, still more preferably at most 3 wt.-%, most preferably at most 2 wt.-% and in particular at most 1 wt.-%. A skilled person is fully aware of methods that are suitable to determine the degree of amorphicity, e.g. quantitative XRPD.

The method according to the invention is directed to the preparation of amorphous silibinin. The method according to the invention is no synthetic chemical method preparing amorphous silibinin from suitable building blocks, but a physical isolation procedure that aims at providing the drug silibinin, which is already contained in the starting material (preferably milk thistle fruits), in a purity as high as possible and converting it into an amorphous state.

A skilled person is aware the extracts from natural sources are usually not absolutely pure (100.00%). Rather, depending upon the efficiency of the individual purification steps, minor amounts of impurities may still be present in the final product. In this context, the method according to the invention may be regarded as being directed to the preparation of an extract from milk thistle fruits, the extract being provided in amorphous state and comprising a high content of silibinin.

The amorphous silibinin that is obtainable by the method according to the invention is distinguished from other amorphous silibinin preparations that are known from the prior art e.g. in that it has a different content of such impurities and/or a better release rate. D. Y-W. Lee et al., J. Nat. Prod. 2003, 66, 1171-4 is silent on the amorphous degree of the material that is obtained. In fact, in both extractions, in the isolation and as well in the results of the X-ray diffraction structure determination for silibinin, it is defined as crystalline in the monoclinic system, but not as amorphous.

The invention further relates to a medicament composed of an amorphous silibinin according to the invention, or use thereof for treatment and prevention of liver and gall bladder dysfunction, in particular for toxic liver damage (fatty liver, alcohol), hepatoses such as mushroom poisoning, acute liver failure, liver necrosis, liver dystrophy, cirrhosis of the liver, hepatic fibrosis, hepatomegaly, and fatty liver degeneration, liver insufficiency, and hepatitis, preferably viral hepatitis, and in particular hepatitis B or C.

It appears that surprisingly, silibinin and its pharmaceutically tolerable salts can be provided in a substantially amorphous modification that is suitable for the treatment of inflammatory, viral liver diseases, preferably viral hepatitis, in particular of hepatitis C. It appears that therapeutically effective dosages of silibinin can be provided by oral administration of amorphous silibinin, although the route of oral administration substantially differs from the route of parenteral administration, e.g. with respect to first-pass metabolism and the like.

It is known that silibinin shows a pronounced first-pass effect.

The first-pass effect (also known as first-pass metabolism or presystemic metabolism) is a phenomenon of drug metabolism whereby the concentration of a drug is greatly reduced before it reaches the systemic circulation. It is the fraction of lost drug during the process of absorption which is generally related to the liver and gut wall. After a drug is swallowed, it is absorbed by the digestive system and enters the hepatic portal system. It is carried through the portal vein into the therapeutic target organ liver before it reaches the rest of the body. The liver metabolizes many drugs, sometimes to such an extent that only a small amount of active drug emerges from the liver to the rest of the circulatory system. Alternative routes of administration like rectally intravenous, intramuscular, and sublingual avoid the first-pass effect because they allow drugs to be absorbed directly into the systemic circulation.

However, it seems that surprisingly, although being subject to extensive first-pass metabolism, the bioavailability of amorphous silibinin is sufficiently high to provide plasma levels effective against viral hepatitis upon oral administration of comparatively high dosages without causing severe side-effects.

Further, it has been surprisingly found that essentially amorphous silibinin in essentially pure form can be obtained from milk thistle extract by a particular method and can be directly processed to pharmaceutical compositions and dosage forms without further purification or enrichment.

Thus, in, e.g., hepatitis C patients who do not respond (i.e. the so called "non-responders") to immuno-modulatory/antiviral combination therapy such as PEG interferon/ribavirin, which represents nowadays the standard treatment for hepatitis C, as well as in liver transplantation patients, a significant reduction of the virus load can be achieved by administration, preferably by oral administration of amorphous silibinin. It additionally appears that the pre-treatment with amorphous silibinin improves the response of the patients to subsequent administration of interferon and ribavirin.

Furthermore, it has been surprisingly found that upon administration of silibinin reinfection with viral hepatitis can be successfully prevented in patients who will undergo or who have undergone liver transplantation. In this regard, U. P. Neumann, M. Biermer, D. Eurich, P. Neuhaus, T. Berg, "Successful prevention of hepatitis C virus (HCV) liver graft reinfection by silibinin mono-therapy", Journal of Hepatology, 2010 report the first successful prevention of HCV reinfection after orthotopic liver transplantation (OLT) by the administration of silibinin.

This is particularly important because such transplantation patients need to take other medicaments in order to suppress their immune response after liver transplantation. Said other medicaments, due to their undesired side effects, make these patients even less tolerable and susceptible for conventional hepatitis C therapies. It now has been surprisingly found, however, that the adverse effects of silibinin are so weak and seldom that it may be administered to these patients in a sufficient dose that prevents viral reinfection of the transplanted liver.

A further aspect of the invention relates to a pharmaceutical composition comprising amorphous silibinin. The pharmaceutical composition is preferably solid.

For the purpose of the specification "amorphous" preferably means non-crystalline. The skilled person is fully aware of analytical methods that are suitable to distinguish the amorphous modification of silibinin from crystalline modifications of silibinin, e.g. x-ray diffraction.

Preferably, the amorphous silibinin is not present in form of nanoparticles. Preferably, the average particle size of the amorphous silibinin particles is above the limit distinguishing microparticles from nanoparticles. Nanoparticles are not only disadvantageous because of their usually laborious method of manufacture. Rather, there is some incidence that nanoparticles have detrimental effects based on their nanoparticulate size as such. Therefore, according to the present invention, nanoparticles are preferably to be avoided.

For the purpose of the specification "silibinin" preferably refers to the free compound as well as to its pharmacologically acceptable salts. Thus, "amorphous silibinin" shall refer to amorphous free silibinin as well as to amorphous salts of silibinin. Preferably, silibinin is present in its free form, i.e. not as a salt.

Further, for the purpose of the specification, the term "silibinin" preferably relates to silibinin, including all its stereoisomers, e.g., silibinin A and silibinin B, and its/their pharmacologically acceptable salts. However, silibinin derivatives such as silibinin esters are preferably not encompassed by the term "silibinin".

In a preferred embodiment, silibinin A is admixed with silibinin B in any relative weight ratio, e.g., 50±5:50±5. In a preferred embodiment, however, the diastereomeric excess of silibinin A is at least 50% de, more preferably at least 75% de, still more preferably at least 90% de, yet more preferably at least 95% de, most preferably at least 98% de and in particular at least 99% de. In another preferred embodiment, the diastereomeric excess of silibinin B is at least 50% de, more preferably at least 75% de, still more preferably at least 90% de, yet more preferably at least 95% de, most preferably at least 98% de and in particular at least 99% de.

In a preferred embodiment, the content of amorphous silibinin in the pharmaceutical composition is at least 80 wt.-%, based on the total weight of silibinin contained therein. Thus, if for example the pharmaceutical composition contains 87 wt.-% amorphous silibinin, the remainder of 13 wt.-% will be crystalline silibinin. Preferably, the content of amorphous silibinin in the pharmaceutical composition is at least 85 wt.-%, more preferably at least 90 wt.-%, still more preferably at least 92 wt.-%, yet more preferably at least 94 wt.-%, most preferably at least 96 wt.-% and in particular at least 98 wt.-%, based on the total weight of silibinin contained therein. In a particularly preferred embodiment, the total amount of silibinin that is contained in the pharmaceutical composition is substantially pure amorphous silibinin, i.e. 100 wt.-% amorphous silibinin and practically no crystalline silibinin at all.

In a preferred embodiment, the composition according to the invention essentially contains no silidianin and/or no silicristin and/or no isosilibinin. Thus, the pharmaceutical composition according to the invention is to be distinguished from compositions containing silymarin, i.e. the milk thistle extract that contains quite a number of different compounds.

Preferably, the pharmaceutical composition according to the invention contains none of the other constituents of silymarin, neither in amorphous nor in crystalline modification, beside the silibinin.

It seems that these further constituents of silymarin also have a physiological effect (e.g. may cause side effects), but that with respect to the treatment of viral hepatitis, silibinin (or its analogues) is most effective, particularly in reducing the viral load. Thus, when administering silymarin, i.e., a mixture of silibinin, silidianin, silicristin, isosilibinin and other constituents, the overall dose of silymarin has to be comparatively high in order to provide a particular amount of silibinin. For example, when silymarin contains, e.g., 42 wt.-% of silibinin, administration of 125 mg silymarin only provides about 52 mg of silibinin and about 73 mg of further compounds that also have a physiological effect (but not the desired effect). The risk of undesired side effects increases with the dose of a physiologically amorphous silibinin. Thus, as far as the profile of undesired side effects is concerned, administration of 52 mg substantially pure silibinin is superior over administration of 125 mg silymarin having a silibinin content of 42 wt.-% (cf. T. Ding et al., "Determination of active component in silymarin by RP-LC and LC/MS", J. Pharm. Biomed. Anal. 2001, 26(1), 155-161).

The structures of silibinin (silybin), silidianin (silydianin), silicristin (silycristin) and isosilibinin (isosilybin) are displayed here below c.f. D. Y.-W. Lee et al., J. Nat. Prod. 2003, 66, 1171-4; N.-C. Kim et al., Org. Biomol. Chem., 2003, 1, 1684-9):

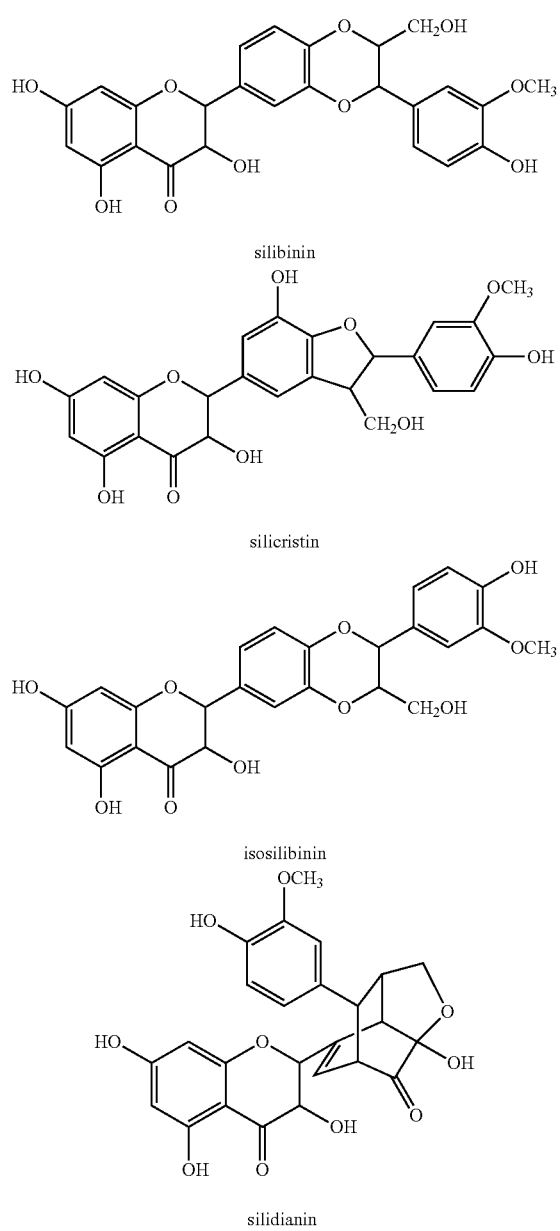

silibinin silicristin isosilibinin silidianin

The invention further relates to a pharmaceutical formulation containing a medicament according to the invention comprising a silibinin according to the invention. Therefore, the invention relates to the preparation of such a medicament or drug and its medical use.

The silibinin according to the invention may be provided in the form of pharmaceutical preparations in dosage units. This means that the preparation may be present in the form of individual portions, for example tablets, dragees, capsules, pills, suppositories, pellets, lozenges, buccal forms, troches, syrups, sachets and ampoules, the amorphous silibinin content of which may correspond to a fraction or a multiple of a single dose. The dosage units may contain, for example, 1, 2, 3, or 4 single doses, or ½, ⅓, or ¼ of a single dose. A single dose preferably contains the quantity of amorphous silibinin which is dispensed in one administration, and which typically corresponds to a whole daily dose or a half, third, or fourth of a daily dose.

A further aspect of the invention relates to a solid pharmaceutical dosage form adapted for oral administration containing the pharmaceutical composition according to the invention.

The preferred embodiments that have been described in connection with the pharmaceutical composition according to the invention also apply to the pharmaceutical dosage form according to the invention and thus, are not repeated hereinafter.

For the purpose of the specification, the term "pharmaceutical dosage form" preferably is synonymous to the terms "medicament", "medication", "administration form" or "dose unit". If, for example, a medicament for oral administration is concerned, for example in the form of a tablet, this tablet is preferably the dose unit to be administered, which contains the dose of the amorphous silibinin intended for the respective time of administration within a particular treatment scheme or regimen. If the dose unit comprises a single tablet, the dose unit corresponds to the administration form. It is also possible, however, for the dose unit to be divided into a number of administration forms, for example a number of tablets, which in each case contain only a partial dose, but in totality the total dose of the amorphous silibinin, which is intended for the respective time of the administration within a treatment scheme (these tablets of the dose unit are then intended for essentially simultaneous administration).

In a preferred embodiment, the pharmaceutical dosage form is formulated for oral administration. Preferably, the pharmaceutical dosage form is an oral administration form selected from the group consisting of tablets, capsules, sugar-coated tablets, pellets, granules, granulates, microparticles, nanoparticles and sachets.

When administering a drug via the oral route, it must be ensured that the bioavailability of the drug from the oral dosage form is sufficiently high. As far as silibinin is concerned, bioavailability of conventional formulations is rather poor and this is one of the fundamental problems that are solved by the present invention. In this respect the limiting factor is the pronounced lipophilicity of silibinin. It appears that surprisingly, providing silibinin as amorphous modification can overcome this limitation without the need to co-formulate silibinin with excipients which interact with silibinin such as cyclodextrins or phospholipids.

In a particularly preferred embodiment, the invention relates to the use of amorphous silibinin for the production of a pharmaceutical dosage form which is formulated for oral administration and essentially contains no silidianin and/or no silicristin and/or no isosilibinin, for the treatment of viral hepatitis, preferably of hepatitis B or C.

Suitable solid dosage forms which are suitable for oral administration (oral administration forms) are known to the person skilled in the art. In this connection, reference can be made in its entirety, for example, to K. H. Bauer et al., Lehrbuch der Pharmazeutischen Technologie [Textbook of Pharmaceutical Technology], WVG Stuttgart 1999.

The oral dosage form is preferably selected from the group consisting of tablets, powders, pellets, granules, sugar-coated tablets, effervescent powders, effervescent granules, effervescent tablets, lyophilizates and capsules. Particularly preferably, the oral dosage form is a tablet, a sugar-coated tablet, granules, pellet or powder, particularly preferably a tablet.

Suitable excipients for the formulation of oral dosage forms are known to the person skilled in the art. In this connection, reference can be made, for example, to H. P. Fiedler, Lexikon der Hilfsstoffe für Pharmazie, Kosmetik and angrenzende Gebiete [Encyclopedia of excipients for pharmacy, cosmetics and related areas], Editio Cantor Aulendorf, 2001.

Nontoxic, inert, pharmaceutically suitable carrier substances are understood to mean solid, semisolid, or liquid diluents, fillers, and formulation adjuvants of all types.

Tablets, dragees, capsules, pills, granules, suppositories, solutions, syrups, suspensions, and emulsions are named as preferred pharmaceutical formulations. Tablets, dragees, capsules, pills, and granules may contain the amorphous silibinin or substances in addition to the customary carrier substances, such as a) fillers and extenders, for example starches, lactose, sucrose, glucose, mannite, and silicic acid, b) binders, for example carboxy-methylcellulose, alginates, gelatins, and polyvinylpyrrolidone, c) humectants, for example glycerin, d) disintegrants, for example agar-agar, calcium carbonate, and sodium carbonate, e) solubility retardants, for example paraffin, f) absorption accelerators, for example quatenary ammonium compounds, g) wetting agents, for example cetyl alcohol and glycerin monostearate, h) adsorbents, for example kaolin and bentonite, and i) lubricants, for example talc, calcium and magnesium stearate, and solid polyethylene glycols, or mixtures of the substances stated under a) through i).

Tablets, dragees, capsules, pills, and granules may be provided with customary coatings and shells optionally containing opacifying agents, and may also have a composition such that they deliver the amorphous silibinin or substances only in the intestinal tract or preferably in a specific portion thereof, optionally in a delayed manner, wherein polymeric substances and waxes, for example, may be used as encapsulating compounds.

The amorphous silibinin or substances may also be present in microencapsulated form, including micro- and nanoparticles, optionally with one or more of the above-referenced carrier substances.

In addition to the amorphous silibinin or substances, suppositories may contain customary water-soluble or water-insoluble carrier substances, for example polyethylene glycols, fats, for example cocoa butter, and higher esters (for example, $C_{14}$ alcohol with $C_{16}$ fatty acid), or mixtures of these substances.

In addition to the amorphous silibinin or substances, solutions and emulsions may contain customary carrier substances such as solvents, solubilizers, and emulsifiers.

In addition to the amorphous silibinin or substances, suspensions may contain customary carrier substances such as liquid diluents. The referenced formulation forms may also contain dyes, preservatives, and fragrance- and taste-enhancing additives, for example peppermint oil and eucalyptus oil, and sweeteners, for example saccharin.

The administration of the medicament comprising silibinin according to the invention can be carried out in any form. The dosage regime might be daily e.g. once, twice, thrice.

Tablets can be obtained, for example, by mixing the amorphous silibinin with known excipients, for example inert diluents, disintegrants, binders, lubricants and/or agents for achieving the depot effect. The tablets can also consist of a number of layers. Apart from the vehicles mentioned, the tablets can also contain additives. Furthermore, glidants can additionally be used for tabletting.

The pharmaceutical dosage form can release the amorphous silibinin immediately or in controlled form.

If the release takes place in controlled form, the release preferably takes place in retarded form. Retarded release is understood according to the invention as preferably meaning a release profile in which the amorphous silibinin is released over a relatively long period of time with a reduced rate of taking with the aim of a prolonged therapeutic action. This is achieved in particular in the case of oral administration. The expression "with at least partially retarded release" according to the invention comprises any pharmaceutical dosage form which guarantees a modified release of the amorphous silibinin contained therein. The pharmaceutical dosage forms are preferably coated or uncoated dosage forms which are produced using special excipients, according to particular processes or by combination of both possibilities, in order to selectively modify the release rate or the site of release. With respect to the time course of release, in the case of the pharmaceutical dosage forms according to the invention the following types are included: delayed release (extended release), repeat action release, prolonged release and sustained release. With respect to further details, reference can be made, for example, to K. H. Bauer et al., Lehrbuch der Pharmazeutischen Technologie [Textbook of Pharmaceutical Technology], 6th edition, WVG Stuttgart, 1999.

Suitable measures for the controlled release of active compound are known to the person skilled in the art. If the pharmaceutical dosage form is an oral dosage form, for example a tablet, a delayed release can be achieved, for example, by embedding the amorphous silibinin in a polymer matrix and/or film coating of the oral dosage form with a membrane.

According to the invention, solid, semisolid or liquid pharmaceutical dosage forms with controlled release behavior can be employed. Solid pharmaceutical dosage forms are preferred, such as, for example, oral osmotic systems (OROS), coated tablets, matrix tablets, multilayer tablets, jacketed tablets, jacketed sugar-coated tablets, diffusion pellets, adsorbates and depot soft gelatin capsules. The oral pharmaceutical dosage form with controlled release of active compound is particularly preferably a coated tablet, jacketed tablet or matrix tablet, particularly preferably a matrix tablet.

The pharmaceutical dosage forms with controlled release of active compound can contain the amorphous silibinin in dissolved, suspended and/or solid, amorphous or crystalline form.

For the production of the pharmaceutical dosage forms according to the invention with controlled release of active compound, the amorphous silibinin can be employed in various particle sizes, e.g. in unground, ground or in micronized form. Preferably, however, the amorphous silibinin is not present in nanoparticulate form.

In the pharmaceutical dosage forms with controlled release of active compound, the amorphous silibinin is preferably present in the form of amorphous silibinin-containing particles, such as, for example, pellets, granules, microcapsules, tablets, extrudates or crystals, which are coated with a diffusion-controlled membrane.

These diffusion-controlled pharmaceutical dosage forms are preferably multiparticulate, i.e. they preferably consist of a multiplicity of coated cores, such as, for example, of neutral pellets, to which a mixture of the amorphous silibinin with a customary binder and thickener is applied, optionally together with customary excipients and vehicles, and are subsequently coated with a diffusion lacquer, the plasticizer and other excipients. The diffusion-controlled pharmaceutical dosage forms according to the invention can moreover consist of homo-geneous cores comprising the amorphous silibinin, which are produced, for example, by granulation, rotor granulation, fluidized bed agglomeration, tabletting, moist extrusion or melt extrusion optionally with spheronization and are coated with a diffusion lacquer which can contain plasticizers and other excipients.

The particles which contain the amorphous silibinin can contain excipients, such as, for example, acids or buffer substances, which modify the pH and thereby contribute in reducing the dependence of the release of the amorphous silibinin on the pH of the release medium.

The diffusion-controlled membrane can moreover contain further excipients which owing to their pH-dependent solubility influence the permeability of the membrane at various pHs and thus contribute in minimizing the pH dependence of the release of the amorphous silibinin.

In addition, the pharmaceutical dosage form with controlled release of the amorphous silibinin can be a coated dosage form which contains one or more swellable excipients which swell strongly on the penetration of liquid through the membrane and cause the coating to tear open as a result of the swelling and volume expansion. As a result of the tearing open of the coating, the release of pharmaceutical from the pharmaceutical dosage form is made possible (pulsatile release).

The coated, diffusion-controlled or pulsatile pharmaceutical dosage forms described can be employed directly and unchanged as a pharmaceutical form. They can, however, also be further processed, optionally with addition of excipients, to give the final dosage form (e.g. capsule, tablet, sachet). In order to achieve a desired release profile, various coated particles can also be combined with one another in a pharmaceutical form, and an administration of an initial dose can take place, for example, by combination with rapidly releasing particles, e.g. uncoated pellets, granules or powders.

Pharmaceutical dosage forms with controlled release which can be used are also formulations which comprise the amorphous silibinin in a matrix. These matrix formulations release the amorphous silibinin by diffusion and/or erosion. Preferably, these pharmaceutical dosage forms are present in the form of a tablet or in the form of a number of tablets which, for example, can be encapsulated. The tablets can be coated or lacquered. Such pharmaceutical dosage forms are produced, for example, by mixing the constituents and direct tabletting, or by dry or moist granulation with subsequent tabletting.

The matrix-forming agents employed can be water-soluble, water-swellable or water-insoluble substances. Preferably, the pharmaceutical dosage forms contain one or more water-swellable polymers.

Furthermore, water-insoluble substances can be employed as structure-forming agents. The pharmaceutical dosage forms can furthermore contain customary tabletting excipients.

Moreover, substances can be incorporated into the matrix which control the pH in the matrix. By the addition of such pH-modifying excipients and/or by the addition of substances which dissolve with increasing pH or dissolve out of the matrix and thus increase the porosity or permeability of the matrix and/or promote the erosion of the matrix, it is possible for these preferred embodiments of the present invention to achieve an almost pH-independent release.

The matrix which contains the amorphous silibinin can also be present in special geometric forms in which the release is influenced by the special geometry and matrix surface. The matrix surface and release surface can be controlled, for example, by compression to give special formats (e.g. annular tablets), and/or by coating of subareas or application of barrier layers by means of a multilayer press.

Formulations with different release properties can preferably be combined to give a pharmaceutical form in multilayer or jacket-core tablets. For instance, by means of multilayer tablets which comprise a rapid-release layer, or jacket-core tablets having a rapidly releasing jacket the controlled releases according to the invention with high initial release of the amorphous silibinin is achieved, while by means of jacket-core tablets with a rapid-release core an end-accelerated release can be achieved.

A further pharmaceutical dosage form with controlled release of the amorphous silibinin is one wherein the amorphous silibinin is embedded in a matrix consisting of one or more physiologically acceptable excipients by means of a melt process. The release of the amorphous silibinin from these "melt extrudates" takes place by diffusion and/or erosion. Preferably, these formulations with controlled release of the amorphous silibinin are present in the form of granules, pellets or tablets. The forms obtained by melt extrusion, in particular pellets and granules, can be processed to give other pharmaceutical forms, such as, for example, by encapsulation or tabletting, optionally with addition of further pharmaceutically customary excipients. Moreover, the melt extrudates according to the invention can be ground and subsequently employed in this comminuted form for the production of other pharmaceutical dosage forms, such as, for example, matrix tablets. The further processing also comprises the combination of formulations having differing pharmaceutical release, such as, for example, retarded- and rapid-release particles, to give a pharmaceutical dosage form.

The melt extrudates and/or the pharmaceutical forms which are produced from melt extrudates can be coated or lacquered. The melt extrudates are preferably produced by mixing the amorphous silibinin with at least one fusible physiologically acceptable excipient (carrier) and optionally further customary additional pharmaceutical substances, melting at a temperature in the range from 50 to 250° C., preferably 60 to 200° C., injection molding or extruding and shaping. In the course of this, the mixing of the components can take place either before the melting or during the melting, or some of the components are melted and the other constituents added to this melt. The mixture of the vehicle, the amorphous silibinin and optionally present additional substances are thermoplastically deformable and can therefore be extruded. Numerous methods suggest themselves for the shaping of the mixture, for example hot granulation, cold granulation, calendering, extrusion and deformation of the still plastic strand or rounding.

In addition to the amorphous silibinin, carrier(s) and optionally plasticizer(s), the extrudable mixture can contain yet other pharmaceutically customary additional substances, for example lubricants and mold-release agents, glidants and flow agents, fillers and adsorbents, stabilizers, free radical traps, complexing agents, antioxidants, photostabilizers, propellants, surfactants, preservatives, colorants, sweeteners and flavorings.

The pharmaceutical dosage forms with controlled release of the amorphous silibinin can also be melt extrudates which contain excipients with pH-modifying properties and/or pH-dependent solubility. By means of these excipients (for example the acids, bases, buffer substances and enteric polymers already described beforehand), it is possible to minimize the pH dependence of the amorphous silibinin release.

In the production of the melt extrudates the formation of "solid solutions" can occur, in which the amorphous silibinin is present in the matrix in molecularly disperse form.

The pharmaceutical dosage forms with controlled release of the amorphous silibinin can also be osmotic pharmaceutical release systems. In principle, osmotic systems of this type are known in the prior art. Here, the pharmaceutical release from the pharmaceutical form is in general based on an osmotic pressure as a driving force.

Preferably, the pharmaceutical dosage form is formulated for once daily (q.d.), twice-daily (b.i.d.), three times (thrice) daily (t.i.d.) or four-times daily administration.

In a preferred embodiment, at least 75% by weight of the originally contained amorphous silibinin have been released from the pharmaceutical dosage form after 1 h under in vitro conditions. Suitable conditions for the determination of the in vitro release of amorphous silibinins are known to the person skilled in the art. In this connection, reference can be made, for example, to the European Pharmacopeia. Preferably, the determination of the release is carried out with the aid of a blade stirrer apparatus in artificial gastric juice (buffer pH 1.2) or artificial intestinal juice (buffer pH 7.6). The amount of the amorphous silibinin released can be analyzed, for example, with the aid of HPLC and UV detection.

In a preferred embodiment, the oral dosage forms are immediate release dosage forms, i.e. the amorphous silibinin is rapidly released therefrom thereby leading to a rapid onset of the drug in the gastrointestinal tract. In a preferred embodiment, 30 minutes after administration of the oral dosage form, at least 75 wt.-%, more preferably at least 80 wt.-%, still more preferably at least 85 wt.-%, most preferably at least 90 wt.-% and in particular at least 95 wt.-% of the originally contained amorphous silibinin have been released from the oral dosage form.

In another preferred embodiment, 0.5 to 75% by weight of the originally contained amorphous silibinin have been released from the pharmaceutical dosage form after 1 h under in vitro conditions.

Preferred release profiles $A_1$ to $A_8$ are summarized in the following table:

and the absorption processes and thus the absorption can be improved overall. The terpenes can be natural or synthetic ethereal oils and/or their terpenoid constituents in the form of the pure substances or mixtures or derivatives of these pure substances. Among the ethereal oils, mention may be made in particular of thyme oil, eucalyptus oil, pine needle oil, tea tree oil, cajeput oil, cardamon oil, peppermint oil, sage oil and rosemary oil, preferably thyme oil. For the terpenes as substances which are also intended to include terpenoid substances, mention may be made in particular of the hemiterpenes such as, for example, isoprene, tiglic acid, angelic acid, isovaleric acid; the monoterpenes, including the acyclic monoterpenes such as, for example, 2,6-dimethyloctane, α-myrcene, (E)-p-ocimene, perillene, linalool, geranial, (S)-(+)citronellal and the monocyclic monoterpenes such as, for example, cyclo-propane monoterpenes and cyclobutane monoterpenes such as chrysanthemic acid or junionone, cyclopentane monoterpenes such as, for example, iridoids or nepetalactones or (−)-secologanin and (−)-oleuropein, cyclohexane monoterpenes such as o-menthane, cis- or trans-p-menthane, (R)-(+)-limonene, terpinols, (−)-menthol, (+)-perillaaldehyde, (−)-menthone or (+)-carvone, bicyclic monoterpenes such as the oxygen-bridged terpenes 1,4-cineol, 1,8-cineol, or ascaridol; the cyclopropane bicycles carane and thujane, the cyclobutane bicycle pinane, and the bicycloheptanes camphane and fenchane; the sesqui-terpenes such as framesane, bisabolane, germacrane elemane, and humulane. Particularly preferred terpenes are thymol, menthol, cineol, borneol, carvone, limenone and pinene, usually preferably thymol.

| after [h] | $A_1$ % by wt. | $A_2$ % by wt. | $A_3$ % by wt. | $A_4$ % by wt. | $A_5$ % by wt. | $A_6$ % by wt. | $A_7$ % by wt. | $A_8$ % by wt. |
|---|---|---|---|---|---|---|---|---|
| 0.5 | 5.0-34 | 6.0-33 | 7.0-32 | 9.0-31 | 11-30 | 13-30 | 15-29 | 17-28 |
| 1 | 12-53 | 15-52 | 18-50 | 20-48 | 22-46 | 24-44 | 27-42 | 30-40 |
| 2 | 25-74 | 27-71 | 29-68 | 31-65 | 33-62 | 36-60 | 39-58 | 42-56 |
| 3 | 33-85 | 36-82 | 39-79 | 42-76 | 45-73 | 48-71 | 50-69 | 52-67 |
| 4 | 41-92 | 44-89 | 47-86 | 50-83 | 53-81 | 55-79 | 58-77 | 60-75 |
| 6 | 52-98 | 55-97 | 58-96 | 60-94 | 63-92 | 66-90 | 69-88 | 72-86 |
| 8 | >62 | >65 | >68 | 71-99 | 74-98 | 76-98 | 78-97 | 80-97 |
| 12 | >70 | >73 | >76 | >79 | >82 | >84 | >86 | >88 |

In a preferred embodiment, the pharmaceutical dosage form contains amorphous silibinin in combination with a cyclodextrin and/or a phospholipid.

Pharmaceutical formulations which contain silibinin and cyclodextrins are known in the prior art (cf., for example, EP 422 497). Preferably, the silibinin forms an inclusion complex with the cyclodextrin. Preferred cyclodextrins are α-, β- and γ-cyclodextrins, their O—$C_1$-$C_4$-alkyl and hydroxy-$C_1$-$C_4$-alkyl derivatives.

Pharmaceutical formulations which contain silibinin and phospholipids are likewise known in the prior art (cf. U.S. Pat. No. 4,764,508). Preferably, the silibinin forms a complex with the phospho-lipid. Preferred phospholipids are phosphatidylcholine, phosphatidylethanolamine and phosphatidylserine. Preferred silibinin phospholipid complexes are ternary complexes additionally containing vitamin E (α-tocopherol). Complexes of this type are known from the prior art as "SPV complexes" (cf. A Federico, Gut. 2006, 55(6), 901-2).

In addition to the amorphous silibinin, the pharmaceutical dosage form can contain one or more terpenes. By means of the action of the terpene, both the absorption requirements The pharmaceutical dosage form contains amorphous silibinin. Silibinin is a constituent of silymarin. Preferably, in addition to amorphous silibinin, the pharmaceutical dosage form contains none of the other constituents of silymarin. Furthermore, the pharmaceutical dosage form preferably contains no pharmaceutical excipients that interact with silibinin, e.g. that form complexes with silibinin, such as cyclodextrins or phospholipids.

Preferably, one or more of the substances selected from the group consisting of isosilibinin, silidianin, silicristin, taxifolin, isosilicristin, silimonin, silandrin, silihermin and neosilihermin is not contained in the pharmaceutical dosage form, i.e. the pharmaceutical dosage form is preferably essentially free of at least one of the above mentioned substances. In this connection, "essentially free" means that the residual contents of the substance concerned is preferably less than 2.0% by weight, more preferably less than 1.0% by weight, even more preferably less than 0.5% by weight, most preferably less than 0.1% by weight and in particular less than 0.05% by weight, based on the total weight of the pharmaceutical dosage form. Analytical methods for the determination of the residual content of these substances are known to the person skilled in the art, for example HPLC.

It has been found that the individual constituents of silymarin differ in their chemical and physical properties and contribute to the pharmacological activity of silymarin to a very different extent such that it is advantageous to administer silibinin or its derivatives and/or salts as the only constituent of silymarin, i.e. uniquely. It appears that in this way both the efficacy and the patient compliance can be improved.

Furthermore, it has been surprisingly found that the tolerability of the various constituents of silymarin differs from one another and that silibin is more tolerable, particularly less toxic, than silymarin (i.e. than the mixture containing other compounds besides silibinin).

In a preferred embodiment, the pharmaceutical dosage form contains the amorphous silibinin preferably in a dose of at least 10 mg, at least 15 mg, at least 20 mg, at least 25 mg, at least 50 mg, at least 75 mg, at least 100 mg, at least 125 mg, at least 150 mg, at least 175 mg or at least 200 mg; more preferably at least 225 mg, at least 250 mg, at least 275 mg, at least 300 mg, at least 325 mg, at least 350 mg, at least 375 mg or at least 400 mg; even more preferably at least 425 mg, at least 450 mg, at least 475 mg, at least 500 mg, at least 525 mg, at least 550 mg, at least 575 mg or at least 600 mg; most preferably at least 625 mg, at least 650 mg, at least 675 mg, at least 700 mg, at least 725 mg, at least 750 mg, at least 775 mg or at least 800 mg; and in particular at least 825 mg, at least 850 mg, at least 875 mg, at least 900 mg, at least 925 mg, at least 950 mg, at least 975 mg, or at least 1000 mg.

In another preferred embodiment, the pharmaceutical dosage form contains the amorphous silibinin preferably in a dose of at least 1050 mg, at least 1100 mg, at least 1150 mg, at least 1200 mg or at least 1250 mg; more preferably at least 1300 mg, at least 1350 mg, at least 1400 mg, or at least 1450 mg; still more preferably at least 1500 mg, at least 1550 mg, at least 1600 mg, at least 1650 mg, or at least 1700 mg; most preferably at least 1750 mg, at least 1800 mg, at least 1850 mg, at least 1900 mg, at least 1950 mg, or at least 2000 mg.

In case that the dosage is too high in order to be swallowed by a subject when incorporated in a single pharmaceutical dosage form, the skilled person is fully aware that the corresponding dose can be divided into two or more sub-portions that are incorporated into two or more pharmaceutical dosage forms which then are adapted for simultaneous administration.

The pharmaceutical dosage form contains the amorphous silibinin preferably in a dose of at least 1.0 mg/kg, more preferably at least 2.5 mg/kg, even more preferably at least 5.0 mg/kg, most preferably at least 7.5 mg/kg and in particular at least 10 mg/kg, at least 12.5 mg/kg, at least 15 mg/kg, at least 17.5 mg/kg, at least 20 mg/kg, at least 22.5 mg/kg, at least 25 mg/kg, at least 27.5 mg/kg or at least 30 mg/kg, based on the bodyweight of the patient. Preferably, said dose is a daily dose. Thus, when the pharmaceutical dosage form is adapted for, e.g., administration twice daily, the respective daily dose is divided into two portions of identical amount. Analogously, when the pharmaceutical dosage form is adapted for, e.g., administration thrice daily, the respective daily dose is divided into three portions of identical amount.

In a preferred embodiment, the daily dose of the amorphous silibinin is at least 5, more preferably at least 10, still more preferably at least 15 and most preferably at least 20 mg per kg body weight.

In a preferred embodiment, the daily dose of the amorphous silibinin is 20 mg per kg body weight. Thus, when the pharmaceutical dosage form is adapted for administration once daily, it preferably contains the entire amount of the amorphous silibinin, e.g. 1400 mg amorphous silibinin for a patient having a body weight of 70 kg. When the pharmaceutical dosage form is adapted for administration twice daily, it preferably contains half the amount of the amorphous silibinin, e.g., 700 mg amorphous silibinin for a patient having a body weight of 70 kg. When the pharmaceutical dosage form is adapted for administration thrice daily, it preferably contains a third of the amount of the amorphous silibinin, e.g., amorphous 467 mg silibinin for a patient having a body weight of 70 kg. When the pharmaceutical dosage form is adapted for administration four times daily, it preferably contains a quart of the amount of the amorphous silibinin, e.g., amorphous 350 mg silibinin for a patient having a body weight of 70 kg.

In a preferred embodiment, the pharmaceutical dosage form is adapted for administration once, twice, thrice or four times daily so that the overall daily dose of amorphous silibinin that is administered when administering the pharmaceutical dosage form in the prescribed mode, amounts to at least 300 mg, at least 325 mg, at least 350 mg, at least 375 mg or at least 400 mg; more preferably at least 425 mg, at least 450 mg, at least 475 mg, at least 500 mg, at least 525 mg, at least 550 mg, at least 575 mg or at least 600 mg; still more preferably at least 625 mg, at least 650 mg, at least 675 mg, at least 700 mg, at least 725 mg, at least 750 mg, at least 775 mg or at least 800 mg; yet more preferably at least 825 mg, at least 850 mg, at least 875 mg, at least 900 mg, at least 925 mg, at least 950 mg, at least 975 mg, or at least 1000 mg; most preferably at least 1050 mg, at least 1100 mg, at least 1150 mg, at least 1200 mg or at least 1250 mg; and in particular at least 1300 mg, at least 1350 mg, at least 1400 mg, at least 1450 mg or at least 1500 mg.

In another preferred embodiment, the pharmaceutical dosage form is adapted for administration once, twice, thrice or four times daily so that the overall daily dose of amorphous silibinin that is administered when administering the pharmaceutical dosage form in the prescribed mode, amounts to at least 1000 mg, at least 1050 mg, at least 1100 mg, at least 1150 mg or at least 1200 mg; more preferably at least 1250 mg, at least 1300 mg, at least 1350 mg, at least 1400 mg, at least 1450 mg, at least 1500 mg, at least 1550 mg or at least 1600 mg; still more preferably at least 1650 mg, at least 1700 mg, at least 1750 mg, at least 1800 mg, at least 1850 mg, at least 1900 mg, at least 1950 mg or at least 2000 mg; yet more preferably at least 2050 mg, at least 2100 mg, at least 2150 mg, at least 2200 mg, at least 2250 mg, at least 2300 mg, at least 2350 mg, or at least 2400 mg; most preferably at least 2450 mg, at least 2500 mg, at least 2550 mg, at least 2600 mg or at least 2650 mg; and in particular at least 2700 mg, at least 2750 mg, at least 2800 mg, at least 2850 mg, at least 2900 mg, at least 2950 mg or at least 3000 mg.

In a preferred embodiment, after a single oral administration, the pharmaceutical dosage form according to the invention provides maximal serum concentrations $C_{max}$ for free silibinin (free=neither metabolized nor bound to plasma proteins, silibinin A+silibinin B) of at least 5000 ng/mL or at least 6000 ng/mL, more preferably at least 7000 ng/mL or at least 8000 ng/mL, still more preferably at least 9000 ng/mL or at least 10,000 ng/mL, yet more preferably at least 11,000 ng/mL or at least 12,000 ng/mL, most preferably at least 13,000 ng/mL or at least 14,000 ng/mL and in particular at least 15,000 ng/mL or at least 16,000 ng/mL.

In a preferred embodiment, after a single oral administration, the pharmaceutical dosage form according to the invention provides maximal serum concentrations $C_{max}$ for free silibinin A (free=neither metabolized nor bound to plasma proteins) of at least 1000 ng/mL or at least 1500 ng/mL, more preferably at least 2000 ng/mL or at least 2500 ng/mL, still more preferably at least 3000 ng/mL or at least 4000 ng/mL, yet more preferably at least 5000 ng/mL or at least 6000 ng/mL, most preferably at least 7000 ng/mL or at least 8000 ng/mL and in particular at least 9000 ng/mL or at least 10,000 ng/mL.

In a preferred embodiment, after a single oral administration, the pharmaceutical dosage form according to the invention provides maximal serum concentrations $C_{max}$ for free silibinin B (free=neither metabolized nor bound to plasma proteins) of at least 1250 ng/mL or at least 1500 ng/mL, more preferably at least 1750 ng/mL or at least 2000 ng/mL, still more preferably at least 2250 ng/mL or at least 2500 ng/mL, yet more preferably at least 2750 ng/mL or at least 3000 ng/mL, most preferably at least 3250 ng/mL or at least 3500 ng/mL and in particular at least 3750 ng/mL or at least 4000 ng/mL.

In a preferred embodiment, after a single oral administration, the pharmaceutical dosage form according to the invention provides an area under the curve $AUC_t$ for free silibinin (free=neither metabolized nor bound to plasma proteins, silibinin A+silibinin B) of at least 5000 ng/h/mL or at least 6000 ng/h/mL, more preferably at least 7000 ng/h/mL or at least 8000 ng/h/mL, still more preferably at least 9000 ng/h/mL or at least 10,000 ng/h/mL, yet more preferably at least 11,000 ng/h/mL or at least 12,000 ng/h/mL, most preferably at least 13,000 ng/h/mL or at least 14,000 ng/h/mL and in particular at least 15,000 ng/h/mL or at least 16,000 ng/h/mL.

In a preferred embodiment, after a single oral administration, the pharmaceutical dosage form according to the invention provides an area under the curve $AUC_t$ for free silibinin A (free=neither metabolized nor bound to plasma proteins) of at least 3000 ng/h/mL or at least 4000 ng/h/mL, more preferably at least 5000 ng/h/mL or at least 6000 ng/h/mL, still more preferably at least 7000 ng/h/mL or at least 8000 ng/h/mL, yet more preferably at least 9000 ng/h/mL or at least 10,000 ng/h/mL, most preferably at least 11,000 ng/h/mL or at least 12,000 ng/h/mL and in particular at least 13,000 ng/h/mL or at least 14,000 ng/h/mL.

In a preferred embodiment, after a single oral administration, the pharmaceutical dosage form according to the invention provides an area under the curve $AUC_t$ for free silibinin B (free=neither metabolized nor bound to plasma proteins) of at least 1000 ng/h/mL or at least 1200 ng/h/mL, more preferably at least 1400 ng/h/mL or at least 1600 ng/h/mL, still more preferably at least 1800 ng/h/mL or at least 2000 ng/h/mL, yet more preferably at least 2500 ng/h/mL or at least 3000 ng/h/mL, most preferably at least 3500 ng/h/mL or at least 4000 ng/h/mL and in particular at least 4500 ng/h/mL or at least 5000 ng/h/mL.

In a preferred embodiment, after regular oral administration in the prescribed manner, e.g. once, twice or thrice daily, for at least seven consecutive days, the pharmaceutical dosage form according to the invention provides average serum concentrations $C_{av}$ for free silibinin (free=neither metabolized nor bound to plasma proteins, silibinin A+silibinin B) of at least 150 ng/mL, more preferably at least 170 ng/mL, still more preferably at least 180 ng/mL, yet more preferably at least 190 ng/mL, most preferably at least 200 ng/mL and in particular at least 210 ng/mL.

In another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin (total=free+metabolized+bound to plasma proteins, silibinin A+silibinin B) of at least 7000 ng/mL, more preferably at least 8000 ng/mL, still more preferably at least 8500 ng/mL, yet more preferably at least 9000 ng/mL, most preferably at least 9500 ng/mL and in particular at least 9750 ng/mL.

In still another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin (total=free+metabolized+bound to plasma proteins, silibinin A+silibinin B) of at least 25,000 ng/mL, more preferably at least 30,000 ng/mL, still more preferably at least 35,000 ng/mL, yet more preferably at least 40,000 ng/mL, most preferably at least 45,000 ng/mL and in particular at least 47,500 ng/mL.

In a preferred embodiment, after continued oral administration in the prescribed manner, e.g. once, twice or thrice daily, for at least seven consecutive days, the pharmaceutical dosage form according to the invention provides average serum concentrations $C_{av}$ for free silibinin A (free=neither metabolized nor bound to plasma proteins) of at least 110 ng/mL, more preferably at least 130 ng/mL, still more preferably at least 150 ng/mL, yet more preferably at least 155 ng/mL, most preferably at least 160 ng/mL and in particular at least 165 ng/mL.

In another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin A (total=free+metabolized+bound to plasma proteins) of at least 2000 ng/mL, more preferably at least 2500 ng/mL, still more preferably at least 2750 ng/mL, yet more preferably at least 3000 ng/mL, most preferably at least 3250 ng/mL and in particular at least 3500 ng/mL.

In still another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin A (total=free+metabolized+bound to plasma proteins) of at least 10,000 ng/mL, more preferably at least 15,000 ng/mL, still more preferably at least 20,000 ng/mL, yet more preferably at least 22,500 ng/mL, most preferably at least 25,000 ng/mL and in particular at least 27,500 ng/mL.

In a preferred embodiment, after continued oral administration in the prescribed manner, e.g. once, twice or thrice daily, for at least seven consecutive days, the pharmaceutical dosage form according to the invention provides average serum concentrations $C_{av}$ for free silibinin B (free=neither metabolized nor bound to plasma proteins) of at least 20 ng/mL, more preferably at least 25 ng/mL, still more preferably at least 30 ng/mL, yet more preferably at least 35 ng/mL, most preferably at least 38 ng/mL and in particular at least 40 ng/mL.

In another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin B (total=free+metabolized+bound to plasma proteins) of at least 4500 ng/mL, more preferably at least 5000 ng/mL, still more preferably at least 5500 ng/mL, yet more preferably at least 5750 ng/mL, most preferably at least 6000 ng/mL and in particular at least 6250 ng/mL.

In still another preferred embodiment, after continued oral administration in the prescribed manner, e.g. once, twice or thrice daily, for at least seven consecutive days, the pharmaceutical dosage form according to the invention provides average serum concentrations $C_{av}$ for total silibinin B (total=free+metabolized+bound to plasma proteins) of at least 7,500 ng/mL, more preferably at least 10,000 ng/mL, still more preferably at least 12,000 ng/mL, yet more preferably at least 14,000 ng/mL, most preferably at least 16,000 ng/mL and in particular at least 18,000 ng/mL.

The skilled person is fully aware how to measure $C_{av}$ for free silibinin A and B as well as total silibinin A and B, respectively.

In a preferred embodiment, after continued oral administration in the prescribed manner, e.g. once, twice or thrice daily, for at least seven consecutive days, the pharmaceutical dosage form according to the invention provides maximal serum concentrations $C_{max}$ for free silibinin (free=neither metabolized nor bound to plasma proteins, silibinin A+silibinin B) of at least 300 ng/mL, more preferably at least 325 ng/mL, still more preferably at least 350 ng/mL, yet more preferably at least 375 ng/mL, most preferably at least 400 ng/mL and in particular at least 425 ng/mL.

In another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin (total=free+metabolized+bound to plasma proteins, silibinin A+silibinin B) of at least 12,500 ng/mL, more preferably at least 14,000 ng/mL, still more preferably at least 15,000 ng/mL, yet more preferably at least 16,000 ng/mL, most preferably at least 16,500 ng/mL and in particular at least 16,750 ng/mL.

In still another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin (total=free+metabolized+bound to plasma proteins, silibinin A+silibinin B) of at least 100,000 ng/mL, more preferably at least 110,000 ng/mL, still more preferably at least 120,000 ng/mL, yet more preferably at least 130,000 ng/mL, most preferably at least 140,000 ng/mL and in particular at least 150,000 ng/mL.

In a preferred embodiment, after continued oral administration in the prescribed manner, e.g. once, twice or thrice daily, for at least seven consecutive days, the pharmaceutical dosage form according to the invention provides maximal serum concentrations $C_{max}$ for free silibinin A (free=neither metabolized nor bound to plasma proteins) of at least 150 ng/mL, more preferably at least 200 ng/mL, still more preferably at least 225 ng/mL, yet more preferably at least 250 ng/mL, most preferably at least 275 ng/mL and in particular at least 300 ng/mL.

In another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin A (total=free+metabolized+bound to plasma proteins) of at least 3000 ng/mL, more preferably at least 3500 ng/mL, still more preferably at least 4000 ng/mL, yet more preferably at least 4500 ng/mL, most preferably at least 5000 ng/mL and in particular at least 5500 ng/mL.

In still another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin A (total=free+metabolized+bound to plasma proteins) of at least 60,000 ng/mL, more preferably at least 70,000 ng/mL, still more preferably at least 80,000 ng/mL, yet more preferably at least 85,000 ng/mL, most preferably at least 90,000 ng/mL and in particular at least 95,000 ng/mL.

In a preferred embodiment, after continued oral administration in the prescribed manner, e.g. once, twice or thrice daily, for at least seven consecutive days, the pharmaceutical dosage form according to the invention provides maximal serum concentrations $C_{max}$ for free silibinin B (free=neither metabolized nor bound to plasma proteins) of at least 60 ng/mL, more preferably at least 70 ng/mL, still more preferably at least 80 ng/mL, yet more preferably at least 90 ng/mL, most preferably at least 100 ng/mL and in particular at least 110 ng/mL.

In another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin B (total=free+metabolized+bound to plasma proteins) of at least 6000 ng/mL, more preferably at least 7000 ng/mL, still more preferably at least 8000 ng/mL, yet more preferably at least 9000 ng/mL, most preferably at least 10,000 ng/mL and in particular at least 11,000 ng/mL.

In still another preferred embodiment, after continued oral administration in the prescribed manner, e.g. once, twice or thrice daily, for at least seven consecutive days, the pharmaceutical dosage form according to the invention provides maximal serum concentrations $C_{max}$ for total silibinin B (total=free+metabolized+bound to plasma proteins) of at least 20,000 ng/mL, more preferably at least 30,000 ng/mL, still more preferably at least 40,000 ng/mL, yet more preferably at least 50,000 ng/mL, most preferably at least 65,000 ng/mL and in particular at least 70,000 ng/mL.

The skilled person is fully aware how to measure $C_{max}$ for free silibinin A and B as well as total silibinin A and B, respectively.

In a preferred embodiment, after continued oral administration in the prescribed manner, e.g. once, twice or thrice daily, for at least seven consecutive days, the pharmaceutical dosage form according to the invention provides minimal serum concentrations $C_{min}$ for free silibinin (free=neither metabolized nor bound to plasma proteins, silibinin A+silibinin B) of at least 30 ng/mL, more preferably at least 35 ng/mL, still more preferably at least 40 ng/mL, yet more preferably at least 45 ng/mL, most preferably at least 55 ng/mL and in particular at least 60 ng/mL.

In another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin (total=free+metabolized+bound to plasma proteins, silibinin A+silibinin B) of at least 4000 ng/mL, more preferably at least 4250 ng/mL, still more preferably at least 4500 ng/mL, yet more preferably at least 4750 ng/mL, most preferably at least 5000 ng/mL and in particular at least 5250 ng/mL.

In still another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin (total=free+metabolized+bound to plasma proteins, silibinin A+silibinin B) of at least 5000 ng/mL, more preferably at least 5500 ng/mL, still more preferably at least 6000 ng/mL, yet more preferably at least 6500 ng/mL, most preferably at least 7000 ng/mL and in particular at least 7500 ng/mL.

In a preferred embodiment, after continued oral administration in the prescribed manner, e.g. once, twice or thrice daily, for at least seven consecutive days, the pharmaceutical dosage form according to the invention provides minimal serum concentrations $C_{min}$ for free silibinin A (free=neither metabolized nor bound to plasma proteins) of at least 30 ng/mL, more preferably at least 35 ng/mL, still more preferably at least 40 ng/mL, yet more preferably at least 45 ng/mL, most preferably at least 50 ng/mL and in particular at least 50 ng/mL.

In another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin A (total=free+metabolized+bound to plasma proteins) of at least 1250 ng/mL, more preferably at least 1500 ng/mL, still more preferably at least 1600 ng/mL, yet more preferably at least 1700 ng/mL, most preferably at least 1800 ng/mL and in particular at least 1900 ng/mL.

In still another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin A (total=free+metabolized+bound to plasma proteins) of at least 3000 ng/mL, more preferably at least 3250 ng/mL, still more preferably at least 3500 ng/mL, yet more preferably at least 3800 ng/mL, most preferably at least 4000 ng/mL and in particular at least 4200 ng/mL.

In a preferred embodiment, after continued oral administration in the prescribed manner, e.g. once, twice or thrice daily, for at least seven consecutive days, the pharmaceutical dosage form according to the invention provides minimal serum concentrations $C_{min}$ for free silibinin B (free=neither metabolized nor bound to plasma proteins) of at least 0.5 ng/mL, more preferably at least 1.0 ng/mL, still more preferably at least 1.5 ng/mL, yet more preferably at least 2.0 ng/mL, most preferably at least 2.5 ng/mL and in particular at least 3 ng/mL.

In another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin B (total=free+metabolized+bound to plasma proteins) of at least 2000 ng/mL, more preferably at least 2250 ng/mL, still more preferably at least 2500 ng/mL, yet more preferably at least 2750 ng/mL, most preferably at least 3000 ng/mL and in particular at least 3250 ng/mL.

In still another preferred embodiment, after continued oral administration in the prescribed manner, e.g. once, twice or thrice daily, for at least seven consecutive days, the pharmaceutical dosage form according to the invention provides minimal serum concentrations $C_{min}$ for total silibinin B (total=free+metabolized+bound to plasma proteins) of at least 3000 ng/mL, more preferably at least 3100 ng/mL, still more preferably at least 3200 ng/mL, yet more preferably at least 3300 ng/mL, most preferably at least 3400 ng/mL and in particular at least 3500 ng/mL.

The skilled person is fully aware how to measure $C_{min}$ for free silibinin A and B as well as total silibinin A and B, respectively.

In a preferred embodiment of the invention, the pharmaceutical dosage form containing the amorphous silibinin is adapted for adjunct therapy, preferably to immuno-modulatory/antiviral combination therapies such as interferon/ribovarin (see below).

A further aspect of the invention relates to the use of amorphous silibinin for the production of a solid pharmaceutical dosage form as described above for the treatment of viral hepatitis.

The invention relates to the use of amorphous silibinin for the production of a, preferably virustatic or antiviral, more preferably viral load reducing medicament for the treatment of viral hepatitis, in particular of hepatitis B or C, preferably of chronic or acute hepatitis C virus infections, preferably by oral administration.

The preferred embodiments that have been described above in connection with the pharmaceutical dosage form according to the invention and the pharmaceutical composition according to the invention, respectively, also apply to this aspect of the invention and thus, are not repeated hereinafter.

In a preferred embodiment, the invention relates to the use of amorphous silibinin for the production of a pharmaceutical dosage form which essentially contains no silidianin and/or no silicristin and/or no isosilibinin, for the treatment of viral hepatitis, preferably of hepatitis B or C.

In a preferred embodiment, according to the invention the treatment of the viral hepatitis, in particular hepatitis B or C, is carried out by decreasing the virus load (viral load). It appears that amorphous silibinin is capable of reducing the viral load in hepatitis B or C patients.

In another preferred embodiment according to the invention, the treatment of the viral hepatitis, in particular hepatitis B or C, is carried out in patients who will undergo or have undergone liver transplantation. Patients who have undergone liver transplantation due to viral hepatitis are at risk for reestablishing viral hepatitis in the freshly transplanted liver. Usually, the virus is incompletely removed from the organism when the infected liver is removed upon surgery and the remainder of the viruses retained in the organism can re-infect the freshly transplanted liver. In chronic hepatitic C infected patients re-infection after liver transplantation occurs in 100% of the cases. As it appears that surprisingly, amorphous silibinin is capable of decreasing the virus load, the risk of re-infection after liver transplantation can be substantially reduced by administration, preferably oral administration, of amorphous silibinin.

Forms of viral hepatitis are known to the person skilled in the art.

In viral hepatitis, at present at least six different forms are definitely known: hepatitis A, B, C, D, E and G. The causative organisms of these infections are hepatotropic viruses. They belong to different virus families in each case and have a DNA or RNA genome. Trans-mission takes place either via the food or by the exchange of body fluids such as sperm and blood. Differences are also to be observed between the various forms with respect to the disease course and the severity of the disease. While hepatitis A and E basically occur in acute form, hepatitis B, C and D can lead to chronic courses with, in some cases, severe complications.

For the purpose of the specification, the term "viral hepatitis" preferably comprises hepatitis B and C.

In a preferred embodiment, the treatment is carried out by reducing the virus load of one or more viruses selected from the group consisting of but not limited to genotypes HCV1, HCV2, HCV3, HCV4, HCV5 and HCV6, preferably HCV1.

In a preferred embodiment, the invention relates to the use of amorphous silibinin for the production of a medicament, which is preferably adapted for oral administration, for the treatment of viral hepatitis, preferably hepatitis C, in patients that do not respond to conventional immuno-modulatory/antiviral combination therapy such as ribavirin/interferon therapy ("non-responders") and/or in patients that partially respond to conventional immuno-modulatory/antiviral combination therapy such as ribavirin/interferon therapy ("partial responders") and/or in patients that show a robust initial response followed by rebounds of viral titers during or after therapy ("relapsers") and/or in patients who will undergo or have undergone liver transplantation.

The invention also relates to the treatment of viral hepatitis C by means of amorphous silibinin, which treatment is subsequent to a conventional combination therapy by means of ribavirin/interferon. Preferably, therapy by administration of amorphous silibinin starts after ribavirin/interferon therapy has failed (either initially or after a certain period of treatment).

In the connection with conventional hepatitis C therapy by administration of ribavirin/interferon, the terms "non-responders", "partial responders" and "relapsers" are known to the person skilled in the art. Nowadays, pegylated interferon (="peginterferon") plus ribavirin therapy for hepatitis C virus fails in approximately half of genotype 1 patients. Treatment failure occurs either by nonresponse (minimal declines in viral titer) or relapse (robust initial responses followed by rebounds of viral titers during or after therapy).

For the purpose of the specification, a non-responder is preferably regarded as a patient who does not show a decrease of the viral load by <2 $\log_{10}$ IU/ml (i.e., factor 100) when administering ribavirin/interferon (usually peg-interferon α), preferably for 12 weeks. In a preferred embodiment, non-responders have viral titers declines of ≤2.1 $\log_{10}$ IU/mL and absolute titers of ≥4.62 $\log_{10}$ IU/mL at nadir.

For the purpose of the specification, a partial responder is preferably regarded as a patient who does not show a decrease of the viral load by 2 $\log_{10}$ IU/ml at week 12 with detectable HCV RNA at week 24.

For the purpose of the specification, a relapser is preferably regarded as a patient who has declines in viral titers of ≥2.8 $\log_{10}$ and its absolute titer transiently drops below the detection limit (2.78 $\log_{10}$ IU/mL).

In a preferred embodiment of the invention, the pharmaceutical dosage form containing the amorphous silibinin is adapted for adjunct therapy, preferably to immuno-modulatory/antiviral combination therapies such as interferon/ribavirin (see below).

In a preferred embodiment, in addition to the amorphous silibinin the pharmaceutical dosage form contains a further pharmaceutical, which preferably is suitable for the treatment of inflammatory liver diseases, particularly preferably of viral liver diseases, in particular for the treatment of hepatitis B or C.

Preferably, the further pharmaceutical is selected from the group consisting of liver therapeutics, lipotropics [A0513]; nucleosides, nucleotides, exclusive inhibitors of reverse transcriptase [J05AB]; interferons [L03AB] and monoclonal antibodies to HBV (hepatitis B virus). The notations indicated in square brackets relate to the ATC index, preferably in the German version of 2007.

Particularly preferably, the further pharmaceutical is selected from the group consisting of arginine glutamate, citiolone, epomediol, ornithine oxoglurate, tidiacicarginine, myoinositol, methionine and N-acetyl-methionine, choline, ornithine aspartate, cianidanol, tiopronine, betaine, cyanocobalamin, leucine, laevulose, aciclovir, idoxuridine, vidarabine, ribavirine, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b (peginterferon=pegylated interferon).

In a preferred embodiment, the treatment of the patient with the amorphous silibinin serves for the support and/or preparation of a treatment of viral hepatitis, in particular of hepatitis B or C, following this treatment, with another pharmaceutical which is preferably selected from the group consisting of arginine glutamate, silymarin, citiolone, epomediol, ornithine oxoglurate, tidiacicarginine, myoinositol, methionine and N-acetyl-methionine, choline, ornithine aspartate, cianidanol, tiopronine, betaine, cyanocobalamin, leucine, laevulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b.

Thus, preferably following the treatment of viral hepatitis, in particular of hepatitis B or C, with the pharmaceutical dosage form which contains the amorphous silibinin, the treatment of the viral hepatitis, in particular of hepatitis B or C, with another pharmaceutical dosage form takes place.

In a preferred embodiment, the pharmaceutical dosage form is formulated as a constituent of a sequential treatment, the pharmaceutical dosage form initially being orally administered for a first period, and subsequently another pharmaceutical dosage form being administered for a second period. Preferably, the first period comprises at least 2 days, more preferably at least 3 days, even more preferably at least 4 days, most preferably at least 5 days and in particular at least 6 days. Preferably, the second period comprises more days than the first period. Preferably, the second period comprises at least two days, more preferably at least 3 days, even more preferably at least 4 days, most preferably at least 5 days and in particular at least 6 days. In a particular preferred embodiment, the second pharmaceutical dosage form contains a combination of ribavirin and pegylated interferon alfa and the second period comprises a time of 24 to 48 weeks.

Preferably, the other pharmaceutical dosage form contains one or more pharmaceuticals selected from the group consisting of arginine glutamate, silymarin, citiolone, epomediol, ornithine oxoglurate, tidiacicarginine, myoinositol, methionine and N-acetylmethionine, choline, ornithine aspartate, cianidanol, tiopronine, betaine, cyanocobalamin, leucine, laevulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a, interferon gamma 1b and monoclonal antibodies to HBV, particularly preferably an interferon and/or ribavirin and/or silymarin. If the other pharmaceutical dosage form contains an interferon, this is preferably pegylated interferon alfa (peginterferon alfa-2a or peginterferon alfa-2b).

In a particularly preferred embodiment, the other pharmaceutical dosage form contains one or more pharmaceuticals selected from the group consisting of isosilibinin, silidianin, silicristin, taxifolin, isosilicristin, silimonin, silandrin, silihermin and neosilihermin, more preferably only one pharmaceutical selected from the foregoing list. Preferably, the other pharmaceutical dosage form contains amorphous silibinin as defined in connection with the pharmaceutical dosage form described above which is administered for the first period, and is preferably essentially free of at least one, preferably all, of the above-mentioned substances. In this connection, "essentially free" means that the residual contents of the substance concerned is preferably less than 2.0% by weight, more preferably less than 1.0% by weight, even more preferably less than 0.5% by weight, most preferably less than 0.1% by weight and in particular less than 0.05% by weight, based on the total weight of the pharmaceutical dosage form.

The other pharmaceutical dosage form can in principle be formulated for parenteral or oral administration. According to the invention, it is preferably formulated for oral administration.

In a preferred embodiment, the treating regimen according to the invention comprises two phases which follow one another consecutively, namely a first period and a second period.

Preferably, during the first period the pharmaceutical dosage form containing the amorphous silibinin is administered orally, but no other pharmaceutical dosage form having a hepatic effect is administered simultaneously. During the second period another pharmaceutical dosage form is administered which preferably contains ribavirin and/or pegylated interferon alfa. In a preferred embodiment, the pharmaceutical dosage form containing the amorphous silibinin is also administered during the second period, preferably orally. In another preferred embodiment, the pharmaceutical dosage form containing the amorphous silibinin is not administered during the second period, i.e., only said other pharmaceutical dosage form is administered.

Preferred embodiments $F_1$ to $F_{15}$ of the biphasic treating regimen are summarized in the table here below:

| no. of days | $F_1$ | $F_2$ | $F_3$ | $F_4$ | $F_5$ | $F_6$ | $F_7$ | $F_8$ | $F_9$ | $F_{10}$ | $F_{11}$ | $F_{12}$ | $F_{13}$ | $F_{14}$ | $F_{15}$ |
|---|---|---|---|---|---|---|---|---|---|---|---|---|---|---|---|
| first period | ≥1 | ≥1 | ≥2 | ≥2 | ≥2 | ≥3 | ≥3 | ≥4 | ≥3 | ≥4 | ≥4 | ≥5 | ≥5 | ≥7 | ≥7 |
| second period | ≥1 | ≥2 | ≥1 | ≥2 | ≥3 | ≥2 | ≥3 | ≥3 | ≥4 | ≥4 | ≥5 | ≥4 | ≥5 | ≥7 | ≥14 |

In another preferred embodiment, the treating regimen according to the invention comprises three phases which follow one another consecutively, namely a first period, a second period and a third period. Preferably, during the first period the pharmaceutical dosage form containing the amorphous silibinin is administered orally, but no other pharmaceutical dosage form having a hepatic effect is administered simultaneously. During the second period another pharmaceutical dosage form which preferably contains ribavirin and/or pegylated interferon alfa is administered, and the pharmaceutical dosage form containing the amorphous silibinin is also administered during the second period, preferably orally. Preferably, during the third period said other pharmaceutical dosage form which preferably contains ribavirin and/or pegylated interferon alfa is administered, but the pharmaceutical dosage form containing the amorphous silibinin is not administered during the third period, i.e., only said other pharmaceutical dosage form is administered.

Preferred embodiments $G_1$ to $G_{15}$ of the triphasic treating regimen are summarized in the table here below:

| no. of days | $G_1$ | $G_2$ | $G_3$ | $G_4$ | $G_5$ | $G_6$ | $G_7$ | $G_8$ | $G_9$ | $G_{10}$ | $G_{11}$ | $G_{12}$ | $G_{13}$ | $G_{14}$ | $G_{15}$ |
|---|---|---|---|---|---|---|---|---|---|---|---|---|---|---|---|
| first period | ≥1 | ≥1 | ≥2 | ≥1 | ≥1 | ≥2 | ≥2 | ≥2 | ≥3 | ≥4 | ≥5 | ≥6 | ≥7 | ≥14 | ≥14 |
| second period | ≥1 | ≥2 | ≥1 | ≥1 | ≥2 | ≥2 | ≥1 | ≥2 | ≥3 | ≥4 | ≥5 | ≥6 | ≥7 | ≥7 | ≥14 |
| third period | ≥1 | ≥1 | ≥1 | ≥2 | ≥2 | ≥1 | ≥2 | ≥2 | ≥3 | ≥4 | ≥5 | ≥6 | ≥7 | ≥7 | ≥7 |

In yet another preferred embodiment, the treating regimen according to the invention comprises three phases which follow one another consecutively, namely a first period, a second period and a third period. Preferably, during the first period another pharmaceutical dosage form is administered which preferably contains ribavirin and/or pegylated interferon alfa, and the pharmaceutical dosage form containing the amorphous silibinin is not administered during the first period. During the second period said another pharmaceutical dosage form which preferably contains ribavirin and/or pegylated interferon alfa is still administered, and the pharmaceutical dosage form containing the amorphous silibinin is also administered (co-administered) during the second period orally. Preferably, during the third period said other pharmaceutical dosage form which preferably contains ribavirin and/or pegylated interferon alfa is administered, but the pharmaceutical dosage form containing the amorphous silibinin is not administered during the third period, i.e., only said other pharmaceutical dosage form is administered. In other words, according to this preferred embodiment, said other pharmaceutical dosage form which preferably contains ribavirin and/or pegylated interferon alfa is administered continuously, and during an interim period (=second period) the pharmaceutical dosage form containing the amorphous silibinin is co-administered orally.

Preferred embodiments $H_1$ to $H_{15}$ of the triphasic treating regimen are summarized in the table here below:

| no. of days | $H_1$ | $H_2$ | $H_3$ | $H_4$ | $H_5$ | $H_6$ | $H_7$ | $H_8$ | $H_9$ | $H_{10}$ | $H_{11}$ | $H_{12}$ | $H_{13}$ | $H_{14}$ | $H_{15}$ |
|---|---|---|---|---|---|---|---|---|---|---|---|---|---|---|---|
| first period | ≥1 | ≥1 | ≥2 | ≥1 | ≥1 | ≥2 | ≥2 | ≥2 | ≥3 | ≥4 | ≥5 | ≥6 | ≥7 | ≥14 | ≥14 |
| second period | ≥1 | ≥2 | ≥1 | ≥1 | ≥2 | ≥2 | ≥1 | ≥2 | ≥3 | ≥4 | ≥5 | ≥6 | ≥7 | ≥7 | ≥14 |
| third period | ≥1 | ≥1 | ≥1 | ≥2 | ≥2 | ≥1 | ≥2 | ≥2 | ≥3 | ≥4 | ≥5 | ≥6 | ≥7 | ≥7 | ≥7 |

A further aspect of the invention relates to a pharmaceutical dosage form as described above, preferably adapted for oral administration, for treating or preventing viral hepatitis as described above.

A still further aspect of the invention relates to a kit comprising at least one pharmaceutical dosage form according to the invention, which contains amorphous silibinin, and at least one other pharmaceutical dosage form. Both the pharmaceutical dosage form according to the invention, which contains amorphous silibinin, and the other pharmaceutical dosage form are described above, such that all preferred embodiments analogously also apply for the kit according to the invention.

In a preferred embodiment, the kit contains as many pharmaceutical dosage forms (individual dose units) as are necessary in order to carry out a sequential therapy, the pharmaceutical dosage form which contains the amorphous silibinin initially being administered for a first period and subsequently the other pharmaceutical dosage form being administered for a second period. Preferably, the first period comprises at least 2 days, more preferably at least 3 days, even more preferably at least 4 days, most preferably at least 5 days and in particular at least 6 days. Preferably, the second period comprises more days than the first period. Preferably, the second period comprises at least 2 days, more preferably at least 3 days, even more preferably at least 4 days, most preferably at least 5 days and in particular at least 6 days.

In a particularly preferred embodiment, the invention relates to the use of amorphous silibinin for the production of a pharmaceutical dosage form, which is formulated for oral administration, for the treatment of viral hepatitis C in non-responders with regard to ribavirin/interferon therapy, i.e., in patients who do not respond to immuno-modulatory/antiviral combination therapy such as ribavirin/interferon therapy.

A further aspect of the invention relates to amorphous silibinin, preferably for oral administration, for the treatment of viral hepatitis, preferably hepatitis C. Preferred embodiments of the aspect of the invention become evident from the above description of the preferred embodiments of the other aspects of the invention and thus, are not repeated.

A further aspect of the invention relates to the treatment of viral hepatitis, preferably hepatitis C, comprising the administration, preferably the oral administration, of a pharmaceutically effective amount of amorphous silibinin to a subject in need thereof. Preferred embodiments of the aspect of the invention become evident from the above description of the preferred embodiments of the other aspects of the invention and thus, are not repeated.

The following examples further illustrate the invention but are not to be construed as limiting its scope.

EXAMPLE 1

Full Description of the Claimed Invention in Detail

A.-1 Pre-Degreasing of the Drug 5,000 kg milk thistle fruits are mechanically pre-degreased. Milk thistle fruits are mechanically separated from foreign materials and metallic parts by sieving through a 1 cm sieve and afterwards using a magnetic separator. In a mill which contains 4 rotating rollers, crushing and pressing is carried out at room temperature and 65 bar of pressure. On a screw conveyor the partially degreased milk thistle fruits are warmed at 40-50° C. The yield of this production step is variable depending on the kind and the oil content of the drug.

A.-2. Extraction

The pre-degreased drug is introduced into percolators and is extracted with ethyl acetate at an entrance temperature of 62° C. and 66° C. The extraction is a continuous one. In process-control: Entrance temperature between 62° C. and 66° C. Method: Temperature is checked three times per day (once per shift) and registered in the batch documentation. The water contained in the milk thistle fruits enriches with the time the water content of the extraction solvent ethyl acetate. The maximum water content shall not exceed 35 g/l. If it is necessary an adjustment with ethyl acetate is carried out. In-process control: Water contents KF-titration ≤35.0 g/l. Method: Ph. Eur. 2.5.32—Water micro determination.

B.-1. Filtration/Centrifugation

In order to eliminate residual drug particles, the obtained extract is filtered through a GAF filter (25-50 μm). The obtained extract is transparent. In process-control: Transparency (visual control).

C. Concentration and Purification

In order to eliminate—the ethyl acetate, the water-soluble impurities and the milk thistle oil, the pre-concentrate is concentrated under vacuum with stirring at temperature ≤40° C. in a recipient with water. The phases which are formed in the reactor are separated by decanting. The precipitate is washed with approx. 500 l of hot water. The water temperature at the entrance is 70-80° C. The exceeding water is aspirated. In process-control: Concentration temperature ≤40° C.

D.-1 Solution

A solution having 8-100 g/l of dry residue is prepared dissolving the resulting cake in ethanol (water content 130-180 g/l) according to the solubility of the content. Then it is warmed up to reflux. As soon as the solution is obtained, it is cooled down to <30° C. The solution is adjusted with water or ethanol in order to reach the prescribed water content.

In process control: Water content by KF-titration: 130-180 g/l. Method: Ph. Eur. 2.5.32—Water micro determination. In process control: Dry residue: 8-100 g/l. Method: Ph. Eur. 2.8.16—Dry residue—Tinctures: In a flat-bottomed dish, introduce 2.0 ml of the extract to be examined. Evaporate to dryness on a water-bath and dry in an oven at 100° C. to 105° C. for 3 h. Allow to cool in a desiccator over anhydrous silica gel and weight. Calculate the result in g/l.

D.-2 Degreasing

The ethanol solution is degreased with hexane. Therefore, the ethanol solution is first saturated with hexane and afterwards, in order to eliminate the not dissolved components, it is centrifuged through a chamber separator and filtered through a plate filter). The degreasing is carried out in a counter-current partition column with hexane. The ethanol solution is filtered through a 5 µm bag filter. Hexane is distilled off from the hexane phase. The oily residue is discarded. In-process control: Transparency (visual control). Method: Transparency is visually controlled three times per day.

E. Concentration

The filtered ethanol phase is concentrated in a reactor at a maximum temperature of 65° C. under vacuum and with stirring until a 35-45% of dry residue is obtained. In process-control: Concentration temperature ≤65° C.

F. Filtration

The concentrate is filtered through a membrane press filter. There are two phases: the paste filtrate and liquid. The paste is used in the following steps.

G. Solution of the Solid Filtrate

A solution having 5-10 g/l of dry residue is prepared dissolving the paste in ethanol (water content 130-180 g/l). In process control: Water content by KF-titration: 130-180 g/l (see D).

H. Addition of Activated Charcoal

After solving the paste, approx. 2% of activated charcoal, calculated on dried substance, is added to this solution and the liquid is refluxed, in order to achieve a good mixing.

I.-1 Filtration with Temperature

The product is filtered at temperature between 50-60° C. through a plate filter and goes to the concentration.

I.-2 Concentration and Crystallization

The concentration temperature shall be ≤65° C. under vacuum until to obtain a dry residue of 35-45% and afterwards the concentrate is cooled down to ≤3° C. and crystallized.

J. Filtration

After cooling the product, it passes through a membrane press filter, in order to separate the solid from the residual liquid. Then a sample is taken to know the content of silibinin. If this content is <95% and the sum of isosilibinin, silidianin and silicristin is >1%, the process goes back to the point G.—SOLUTION OF THE SOLID FILTRATE, without adding activated charcoal, until to obtain a content of silibinin ≥95% and a sum of isosilibinin, silidianin and silicristin ≤1%. Determination is carried out using a reversed-phase liquid chromatographic method in accordance with the Ph. Eur.

K.-1. Washing

The substance is washed with cold water.

K.-2. First Drying and Precrushing

The drying of the product is achieved in a vacuum dryer preferably under a pressure from 70 to 1 mbar and at maximum temperature of the dryer jacket ≤80° C. The dried extract is pre-crushed through 1 mm sieve.

L.-1 Final Solution and Filtration.

The pre-crushed silibinin is dissolved in ethanol ≥99.5% (V/V) until a 2%-12% of dry residue is obtained. The solution is warmed up to reflux in a reactor provided with stirring for 30 minutes and immediately is cooled down to 40° C. Following the cooling, the product is filtered through a plate filter.

M.-1 Final Drying and Pre-Crushing

The final drying of the substance is carried out in:

a) an atmosphere dryer (spray dryer) at an inlet temperature of from 180° C. to 200° C. and an outlet temperature of from 80° C. to 120° C., to obtain a dry powder with ethanol content around 5% and water content lower than 1%; or b) concentrated to maximum 20% of dry residue and then dried directly in the reactor, preferably at less than 80° C., more preferably at 50-60° C. under vacuum to obtain a dry powder. The dried extract is pre-crushed through 2 mm sieve.

M.-2 Milling

The product is ground in a pin mill provided with nitrogen, if more than 3% of the obtained product has a particle size is higher than 180 µm, to get a fine amorphous-like powder.

M.-3 Post-Drying

The product is post dried, if necessary, at maximum 80° C. and maximum 40 mbar of pressure to obtain a dry powder with content of residual ethanol below 1% and water content below 3.5%.

M.-3 Final Homogenisation

The milled product is mixed in a cone for 2 h.

EXAMPLE 2

Quantitative XRPD Method for Determination of Crystalline Silibinin in Amorphous Silibinin (Degree of Amorphicity)

A sample of pure crystalline silibinin was prepared by silibinin recrystallization from ethanol. The sample was then resuspended in ethanol and slowly stirred at room temperature for several hours in order to assure complete crystallization of the amorphous phase. From time to time a sample was subjected to XRPD and the area under the peaks at 2-theta: 20.7, 22.3 and 24.5° was measured. When no more increase in the area of these peaks was observed (XRPD spectrum), the sample was filtered, dried and used as crystalline silibinine standard in the following experiments. The XRPD spectrum of this sample is reported in FIG. 1A.

A sample of amorphous silibinin was obtained by spry drying (Buchi mini Spray drier B-290) silibinin dissolved in ethanol at 40° C., with an air flow of 350 L/h, inlet temperature of 100° C. and pump rate 6 mL/min. The obtained amorphous sample was further milled in a ball mill at 30 Hz for 15 min. in order to guarantee complete amorphization. No changes in the XRPD spectrum were observed after and before the milling. The XRPD spectrum of the amorphous Silibinine standard is reported in FIG. 1B.

The standard of amorphous silibinin was further controlled by DSC (DSC 200 F3 Maia Netzsch; 10°/min). In FIG. 2 the DSC of the crystalline silibinine standard (2A) is compared with the DSC of the amorphous silibinine standard (2B). The DSC of mixtures of the silibinine amorphous standard with respectively from 10% to 100% of the crystalline silibinine standard are reported in FIG. 2C. It is evident from the data reported above that the standard of amorphous silibinin used in the XRPD assessment is the pure amorphous.

Figure 3B:
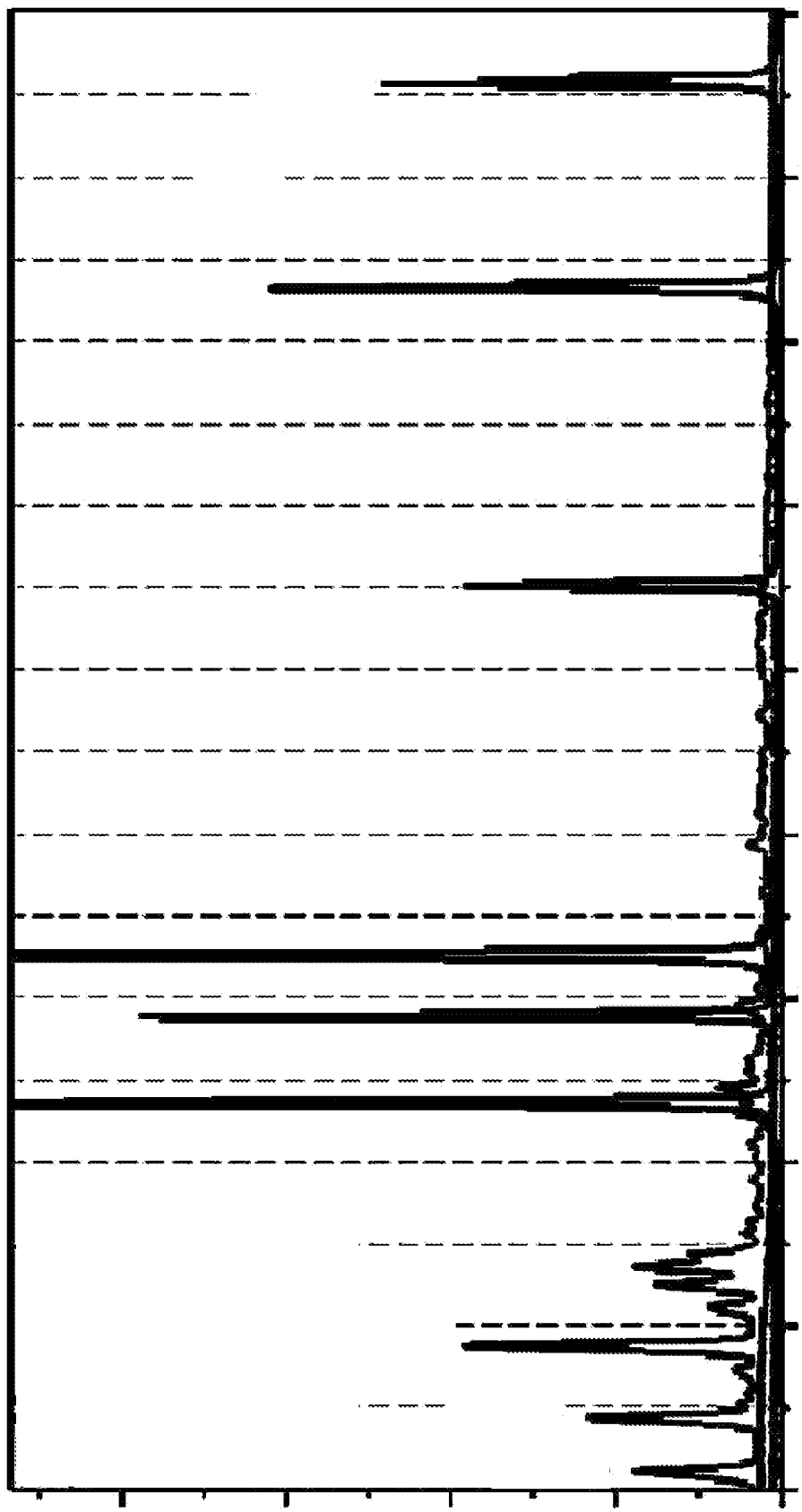
FIG. 3 A: ZnO XRPD spectrum
FIG. 3 B: Referenced peaks for XRPD quantitative assessment
FIG. 3 C: XRPD Spectra of standard mixtures 1-8.

For quantitative XRPD assessment ZnO (XRPD spectrum FIG. 3A) was used as internal standard. Three characteristics peaks of crystalline sylibinin (2-theta: 20.7, 22.3 and 24.5°) were chosen for the quantitative determination of the crystalline form and peaks at 2-theta: 56.6 and 62.8° of the internal standard (IS, ZnO) were used as reference as reported in FIG. 3B.

Eight mixtures of about 250 mg were prepared by mixing 50 mg of the internal standard and X mg of crystalline silibinin and Y mg of amourphous silibinin, provided that X+Y=200 mg. X and Y were varied as reported in the table below:

| sample | internal standard (ZnO; mg) | crystalline silibinin X (mg) | amorphous silibinin Y (mg) | % crystalline |
|---|---|---|---|---|
| Std 1 | 49.94 | 20.02 | 180.07 | 10 |
| Std 2 | 50.05 | 49.96 | 150.05 | 25 |
| Std 3 | 50.09 | 69.98 | 130.07 | 35 |
| Std 4 | 49.91 | 99.91 | 100.08 | 50 |
| Std 5 | 50.09 | 120.01 | 79.98 | 60 |
| Std 6 | 50.03 | 150.01 | 50.16 | 75 |
| Std 7 | 50.10 | 170.07 | 29.96 | 85 |
| Std 8 | 50.08 | 200.11 | — | 100 |

The mixtures were transferred to vials and shaken at room temperature for 1 hour for sample homogenization, using a rotary shaker (FALC F205).

In order to minimize effects due to preferential orientation caused by the habit of the crystalline powder and its positioning on the sample older along with possible dishomogeneity of the sample each sample was positioned on the sample holder an measured three times.

XRPD spectra were obtained using X'Pert diffractometer from PANalytical, using the following parameters for acquisition and data processing:
Wavelength: K$\alpha$1 (A°: 1.540598)
K$\alpha$2 (A°: 1.544426)
K$\alpha$2/K$\alpha$1 intensity ratio: 0.50
Incident beam path, radius 240 mm
X-ray tube: anode Cu, voltage 40 kV, current 40 mA, type: PW3373/00 Cu LFF
Sample movement: spinning (1 s)
Scan axis: gonio
Scan range: 19.9970-65.0004°
Step size: 0.0167°
N of points: 2693
Scan mode: continous
Counting time: 50.165 s
Detector: X'celerator RTMS
PHD lower: 39.5%
PHD upper: 80.0%
Scanning mode, active length 2.122°
AI data were processed by the software TQ analyst 8.0.0.254 using partial least square algorithm (PLS) and the peak ratio normalization.

Three regions were used for quantitative determination (2theta):
20.16-21.00
21.76-22.59
24.02-24.77

For the internal standard the region (2theta): 55.56-63.87 was considered.

Spectra of standard mixtures 1-8 are reported in FIG. 3C.

Figure 4:
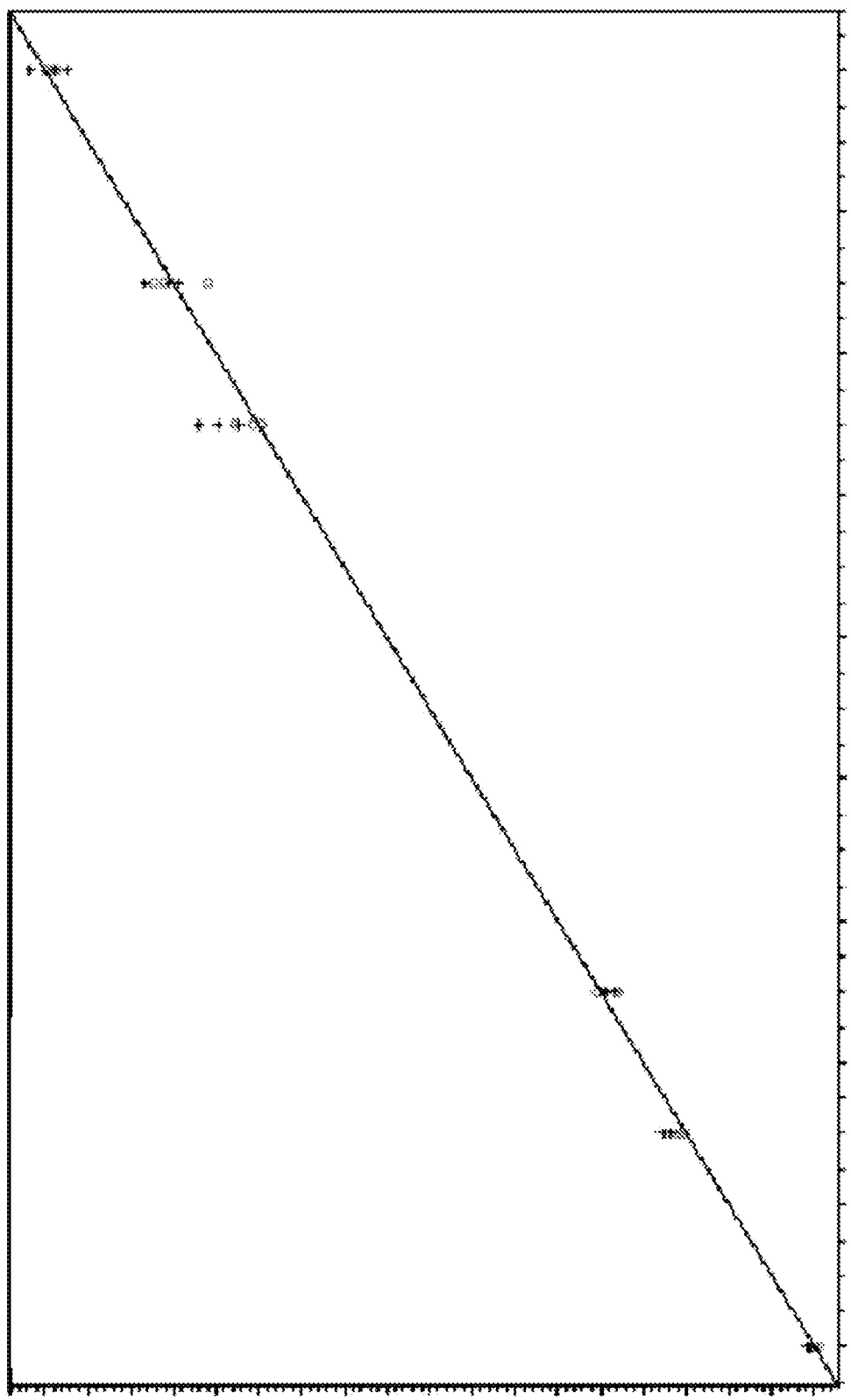
FIG. 4: Quantitative XRPD calibration diagram
FIG. 5 A: XRPD spectrum of 0.25% crystalline silibinin in amorphous silibinin
FIG. 5 B: XRPD spectrum of 0.50% crystalline silibinin in amorphous silibinin
FIG. 5 C: XRPD spectrum of 1.0% crystalline silibinin in amorphous silibinin

All obtained data were processed as above discussed, standard mixtures 4 and 5 were discarded due to difference between calculated and actual value greater than 10%. The resulting calibration diagram for 6 points is reported in FIG. 4. Coefficient of correlation is 0.99904, root mean squared error calibration (RMSEC) is 1.46, recovery is between 95.9 and 108%, repeatability is: C.V. <4.1%, intermediate precision is C.V. <3.0%.

For crystalline silibinin in the amorphous silibinin, the limit of detection (LOD) was found to be 0.5% and the quantitation limit (LOQ) was found to be 1.0%

These parameters were obtained preparing and measuring 0.25, 0.5 and 1% crystalline and amorphous silibinine mixtures, as described above.

XRPD spectra of amorphous silibinin containing respectively 0.25, 0.5 and 1% of crystalline silibinin are reported in FIGS. 5 A, B and C.

These data indicate that this method is able to quantify with very high precision amount from 1% to 100% of crystalline silibinin in the amorphous silibinin using XRPD technique.

EXAMPLE 3

XRPD Assessment of Crystalline Silibinin in Amorphous Silibinin Produced by the Method of this Invention Several lots of silibinin manufactured according to the method of the invention, including steps L and M, were analyzed using the XRPD method described in example 2.

A representative XRPD spectrum of this production of amorphous silibinin is reported in FIG. 6.

Quantitative assessment highlighted crystalline silibinin in the amorphous silibinin to be not more than 5% and typically not detectable or lower than 1%.

Solubility of this product (HPLC—Ph. Eur. 01/2007:2071) after 30 min. is higher than 80%. Conversely the silibinin obtained according to the method of the invention without performing steps L and M, though of high chemical purity is mainly crystalline (typically more than 70% crystalline). A representative XRPD spectrum of the silibinin obtained without performing steps L and M is reported in FIG. 7.

Solubility of this product (HPLC—Ph. Eur. 01/2007:2071) after 30 min. is lower than 80%.

EXAMPLE 4

Stability of the Pure Amorphous Silibinin Obtained According to this Process in Comparison to the Stability of Amorphous Silibinin Contaminated with the Crystalline Compound (XRPD Assessment)

Silibinin samples obtained according to the present invention were stored at 4±2° C. at 60% R.H., 25±2° C. at 60±5% R.H. and 40±2° C. at 60±5% R.H., in a single polyethylene bag for 2 months. After this time the samples were analyzed by XRPD. XRPD spectra for these samples are reported in FIG. 8A. At each condition the pure amorphous was found to be stable.

Conversely the stability of amorphous silibinin samples, containing about 10% of crystalline silibinin gave rise to extended crystallization when stored in a single polyethylene bag for 2 months, 25±2° C. at 60±5% R.H., as can be seen in FIG. 8B.

The invention claimed is:

1. A method for preparing amorphous silibinin comprising the following steps:
   A.) extracting silibinin with ethyl acetate a solvent having a dipole moment of less than 2 Debye,
   B.) separating the solvent phase from solid residues,
   C.) concentrating the solvent phase at a temperature of less than 60° C.,
   D.) combining the concentrate obtained in step C.) with ethanol and then combining it with hexane, concentrating the mixture, and distilling hexane off from said concentrated mixture,
   E.) concentrating the intermediate product obtained in step D.),
   F.) separating the solid phase,
   G.) dissolving the solid phase obtained in step F.) with ethanol,
   H.) adding activated charcoal,
   I.) separating the charcoal from the liquid phase, concentrating the liquid and crystallizing silibinin therefrom,
   J.) separating the crystals obtained in step I.) from the liquid phase, and if required, repeating steps G.), I.), J.) in order to enrich silibinin to a content of more than 95% by weight,
   K.) optionally, filtrating, washing, drying and, if required, repeating these steps,
   L.) combining the material obtained in step K.) with anhydrous alcohol, refluxing, cooling to 40° C., and either concentrating under vacuum or spray drying to obtain an amorphous-like fine powder,
   M.) drying, milling, and homogenizing the obtained amorphous-like fine powder;
   wherein the starting material is milk thistle or a part thereof.

2. The method according to claim 1, wherein step A.) is performed at a temperature of 40-80° C.

3. The method according to claim 2, wherein the temperature is 50-70° C.

4. The method according to claim 1, wherein separating in step B.), F.), I.) and/or J.) is achieved by filtering.

5. The method according to claim 1, wherein concentrating in step C.), D.) and/or L.) and/or drying in step K.) is performed under vacuum.

6. The method according to claim 1, wherein concentrating in step C.) is performed at a temperature of less than 40° C.

7. The method according to claim 1, wherein in step D.) and/or G.) the ethanol is added and the water content is adjusted to 130-180 g/L.

8. The method according to claim 1, wherein concentrating in step E.) is performed at a temperature of less than 65° C.

9. The method according to claim 1, wherein separating in step I.) is performed at a temperature of less than 80° C.

10. The method according to claim 9, wherein the temperature is within the range of 50-60° C.

11. The method according to claim 1, wherein in step L.) the anhydrous alcohol is an anhydrous $C_1$-$C_4$ alcohol.

12. The method according to claim 11, wherein the anhydrous $C_1$-$C_4$ alcohol is ethanol.

13. The method according to claim 1, wherein in step L.) the amorphous-like fine powder is obtained by concentrating under vacuum.

14. The method according to claim 1, wherein in step L.) the amorphous-like fine powder is obtained by spray drying.

* * * * *